US010507227B2

(12) United States Patent
Deber

(10) Patent No.: US 10,507,227 B2
(45) Date of Patent: Dec. 17, 2019

(54) CATIONIC ANTIMICROBIAL PEPTIDES

(71) Applicant: The Hospital for Sick Children, Toronto (CA)

(72) Inventor: Charles M. Deber, Toronto (CA)

(73) Assignee: The Hospital for Sick Children, Ontario (CA)

(*) Notice: Subject to any disclaimer, the term of this patent is extended or adjusted under 35 U.S.C. 154(b) by 0 days.

(21) Appl. No.: 14/687,682

(22) Filed: Apr. 15, 2015

(65) Prior Publication Data

US 2015/0290278 A1   Oct. 15, 2015

Related U.S. Application Data

(60) Provisional application No. 61/979,684, filed on Apr. 15, 2014, provisional application No. 61/983,751, filed on Apr. 24, 2014.

(51) Int. Cl.
| | |
|---|---|
| *A61K 38/10* | (2006.01) |
| *A61K 31/7036* | (2006.01) |
| *A61K 31/407* | (2006.01) |
| *A61K 31/496* | (2006.01) |
| *A61K 38/16* | (2006.01) |

(52) U.S. Cl.
CPC ............ *A61K 38/10* (2013.01); *A61K 31/407* (2013.01); *A61K 31/496* (2013.01); *A61K 31/7036* (2013.01); *A61K 38/16* (2013.01)

(58) Field of Classification Search
CPC .... A61K 38/10; A61K 31/407; A61K 31/496; A61K 31/7036; A61K 38/16
See application file for complete search history.

(56) References Cited

U.S. PATENT DOCUMENTS

| | | | |
|---|---|---|---|
| 3,773,919 A | 11/1973 | Boswell et al. | |
| 4,485,045 A | 11/1984 | Regen | |
| 4,544,545 A | 10/1985 | Ryan et al. | |
| 4,619,794 A | 10/1986 | Hauser | |
| 5,741,516 A | 4/1998 | Webb et al. | |
| 5,811,515 A | 9/1998 | Grubbs et al. | |
| 7,183,059 B2 | 2/2007 | Verdine et al. | |
| 7,192,713 B1 | 3/2007 | Verdine et al. | |
| 7,687,454 B2 * | 3/2010 | Hancock | A61K 38/10 424/1.69 |
| 8,524,669 B2 | 9/2013 | Kufe et al. | |
| 8,586,707 B2 | 11/2013 | Lin et al. | |
| 8,614,186 B2 | 12/2013 | Kufe et al. | |
| 2004/0235745 A1* | 11/2004 | Deber | A61K 38/08 514/2.7 |
| 2011/0144306 A1 | 6/2011 | Verdine et al. | |
| 2011/0236429 A1* | 9/2011 | Hancock | A01N 37/46 424/278.1 |
| 2012/0115793 A1 | 5/2012 | Nash et al. | |
| 2012/0141527 A1 | 6/2012 | Walensky et al. | |
| 2013/0281657 A1 | 10/2013 | Saulnier et al. | |
| 2014/0011746 A1 | 1/2014 | Rapraeger | |
| 2014/0011747 A1 | 1/2014 | Rapraeger | |

FOREIGN PATENT DOCUMENTS

| | | |
|---|---|---|
| CA | 2451310 A1 | 1/2003 |
| DE | 3218121 A1 | 11/1983 |
| EP | 0102324 A2 | 3/1984 |
| EP | 0052322 B1 | 3/1985 |
| EP | 0133988 A2 | 3/1985 |
| EP | 0088046 B1 | 12/1987 |
| EP | 0143949 B1 | 10/1988 |
| EP | 0036676 B2 | 9/1990 |
| EP | 0142641 B1 | 1/1991 |
| EP | 0257956 B2 | 11/2000 |
| EP | 0058481 B2 | 5/2003 |
| JP | 60-007934 | 1/1985 |

OTHER PUBLICATIONS

Kyte and Doolittle, A Simple Method for Displaying the Hydropathic Character of a Protein, J. Mol. Biol. (1982) 157, 105-13.*
Liu and Deber, Guidelines for Membrane Protein Engineering Derived from De Novo Designed Model Peptides, Biopolymers (Peptide Science) 47:41-62, 1998 (supplied in Jul. 19, 2015 IDS).*
Tincu and Taylor, Antimicrobial Peptides from Marine Invertebrates, a Minireview, Antimicrobial Agents and Chemotherapy, Oct. 2004, p. 3645-3654 vol. 48, No. 10.*
Mah et al., A genetic basis for Pseudomonas aeruginosa biofilm antibiotic resistance, Nature | vol. 426 | Nov. 20, 2003, pp. 306-310, see Abstract and p. 307.*
Cirioni et al., In vitro activities of tachyplesin III against Pseudomonas aeruginosa, Peptides 28 (2007) 747-751.*
Cassone and Otvos, Synergy among antibacterial peptides and between peptides and small-molecule antibiotics, Expert Rev. Anti Infect. Ther. 8(16), pp. 703-716, 2010.*
Stapled Peptides for Intracellular Drug Targets, Gregory L. Verdine and Gerard J. Hilinski, Methods in Enzymology, vol. 503, pp. 3-32, 2012.*
Mataraci and Dosler, In Vitro Activities of Antibiotics and Antimicrobial Cationic Peptides Alone and in Combination against Methicillin-Resistant *Staphylococcus aureus* Biofilms, Antimicrobial Agents and Chemotherapy p. 6366-6371 Dec. 2012 vol. 56 No. 12.*

(Continued)

*Primary Examiner* — Karlheinz R. Skowronek
*Assistant Examiner* — Joseph Fischer
(74) *Attorney, Agent, or Firm* — Myers Bigel, P.A.

(57) ABSTRACT

A method for treating an infection comprises administering a peptide in synergistic combination with an antibiotic, wherein the peptide comprises an amino acid sequence with a formula selected from the group consisting of:

$B_{n1}$-Z;                                          (a)

$B_{n1}$-Z-$B_{n2}$; and                            (b)

Z-$B_{n1}$                                           (c)

wherein B is a basic amino acid residue;
n1 and n2 are 1 to 6; and
Z is a sequence of from about 7 to about 24 amino acid residues, said sequence having an average hydrophobicity value of at least 0.3 on the Liu-Deber scale.

9 Claims, 17 Drawing Sheets

Specification includes a Sequence Listing.

(56) References Cited

OTHER PUBLICATIONS

Scott et al., Biological Properties of Structurally Related α-Helical Cationic Antimicrobial Peptides, Infection and Immunity, Apr. 1999, p. 2005-2009.*
Houston et al., Influence of preformed a-helix and a-helix induction on the activity of cationic antimicrobial peptides, Jl. Peptide RES 52, 1998 / 81-88.*
Liu and Deber, Guidelines for Membrane Protein Engineering Derived from De Novo Designed Model Peptides, Biopolymers (Peptide Science), vol. 47, 41-62 (1998), supplied in Jul. 9, 2015 IDS.*
Jenssen et al., Peptide Antimicrobial Agents, Clinical Microbiology Reviews, Jul. 2006, p. 491-511.*
Jiang et al., Effects of Net Charge and the Number of Positively Charged Residues on the Biological Activity of Amphipathic a-Helical Cationic Antimicrobial Peptides, Peptide Science vol. 90 / No. 3 (2007).*
Stark et al., Cationic Hydrophobic Peptides with Antimicrobial Activity, Antimicrob Agents and Chemother., Nov. 2002, p. 3585-3590.*
Chan et al., J. The Journal of Biological Chemistry vol. 279, No. 37, Issue of Sep. 10, pp. 38749-38754, 2004.*
Cirioni et al, Peptides 28 (2007) 747-751.*
Glukhov et al., Biopolymers 89: 360-371, 2008.*
Chan et al., J. the Journal of Biological Chemistry vol. 279, No. 37, Issue of Sep. 10, pp. 38749-38754, 2004 (Year: 2004).*
Glukhov et al, Biopolymers 89: 360-371, 2008 (Year: 2008).*
Allen et al. "Large unilamellar liposomes with low uptake into the reticuloendothelial system", *Febs Lett.* 223(1):42-46 (1987).
Couvreur et al. "Nanocapsules: A New Type of Lysosomotropic Carrier", *Febs Lett.* 84(2):323-323 (1977).
Eppstein et al. "Biological activity of liposome-encapsulated murine interferon γ is mediated by a cell membrane receptor", *Proc. Natl. Acad. Sci. USA* 82:3688-3692 (1985).
Gabizon et al. "Liposome formulations with prolonged circulation time in blood and enhanced uptake by tumors", *Proc. Natl. Acad. Sci. USA* 85:6949-6953 (1988).
Hwang et al. "Hepatic uptake and degradation of unilamellar sphingomyelin/cholesterol liposomes: A kinetic study", *Proc. Natl. Acad. Sci. USA* 77(7):4030-4034 (1980).
Langer et al. "Biocompatibility of polymeric delivery systems for macromolecules", *J. Biomedical Materials Res.* 15:267-277 (1981).
Lasic "Novel applications of liposomes", *TIBTECH* 16:307-321 (1998).
Liu et al. "Guidelines for Membrane Protein Engineering Derived from De Novo Designed Model Peptides", *Biopolymers (Peptide Science)* 47:41-62 (1998).
Sidman et al. "Controlled Release of Macromolecules and Pharmaceuticals from Synthetic Polypeptides Based on Glutamic Acid", *Biopolymers* 22:547-556 (1983).
Yin et al. "Roles of Hydrophobicity and Charge Distribution of Cationic Antimicrobial Peptides in Peptide-Membrane Interactions", *J. Biological Chemistry* 287(10):7738-7745 (2012).

* cited by examiner

CATIONIC ANTIMICROBIAL PEPTIDES

RELATED APPLICATIONS

This application claims the benefit of priority from U.S. Provisional Application Ser. No. 61/979,684 filed Apr. 15, 2014 and U.S. Provisional Application Ser. No. 61/983,751, filed Apr. 24, 2014, the disclosures of each of which are incorporated by reference in their entirety.

STATEMENT REGARDING ELECTRONIC FILING OF A SEQUENCE LISTING

A Sequence Listing in ASCII text format, submitted under 37 C.F.R. § 1.821, entitled 3477-124_ST25.txt, 10,449 bytes in size, generated on Apr. 15, 2015, and filed electronically via EFS-Web, is provided in lieu of a paper copy. The Sequence Listing is incorporated herein by reference into the specification for its disclosures in its entirety.

FIELD OF THE INVENTION

The present invention relates to cationic antimicrobial peptides. More specifically, the present invention is concerned with methods of treating infections and penetrating bacterial biofilms using such peptides alone or in synergistic combination with other antibiotics.

BACKGROUND OF THE INVENTION

Cationic antimicrobial peptides (CAPs) occur naturally as innate immunity agents in a wide spectrum of living organisms including humans, and have become increasingly recognized as templates for prospective antibiotic agents.

Certain cationic antimicrobial peptides, including KKKKKKAAFAAWAAFAA-$NH_2$ (SEQ ID NO:3), are known from CA 2,451,310, where such peptides are described as showing antimicrobial activity against microorganisms including Gram-negative and Gram-positive bacteria.

Yin et al. (JBC, 287:7738-7745, 2012) explain that cationic antimicrobial peptides offer an alternative to conventional antibiotics, as they physically disrupt bacterial membranes, causing cell death. It was shown that peptides designed with high hydrophobicity display strong self-association that is minimized by distribution of positive charges at both peptide termini and it was concluded that balancing peptide hydrophobicity and charge distribution promotes efficient antimicrobial activity.

Bacterial biofilms are surface-attached microbial communities enclosed in extracellular polymeric substance (EPS). Sixty percent of all infectious diseases are caused by biofilms and organisms causing such diseases are up to 4000 times more resistant than the same organism in a free-floating or 'planktonic' state.

There remains a need to identify novel methods of penetrating bacterial biofilms in order to specifically treat or prevent various infectious diseases.

SUMMARY OF THE INVENTION

The present invention relates, in aspects, to methods of treating infection using cationic antimicrobial peptides in synergistic combination with antibiotics. In other aspects, the present invention relates to methods of penetrating bacterial biofilms using cationic antimicrobial peptides.

According to an aspect, there is provided a method for treating an infection, the method comprising administering a peptide in synergistic combination with an antibiotic, wherein the peptide comprises an amino acid sequence with a formula selected from the group consisting of:

(a) $B_{n1}$-Z;

(b) $B_{n1}$-Z-$B_{n2}$; and (c) Z-$B_{n1}$ wherein B is a basic amino acid residue;
n1 and n2 are 1 to 6; and
Z is a sequence of from about 7 to about 24 amino acid residues, said sequence having an average hydrophobicity value of at least 0.3 on the Liu-Deber scale.

In an aspect, the peptide is selected from the group consisting of

| | | |
|---|---|---|
| (a) | KKKKKKXXFXXWXXFXX-$NH_2$; | (SEQ ID NO: 19) |
| (b) | KKKKKKAXFAXWXAFXA-$NH_2$; | (SEQ ID NO: 20) |
| (c) | KKKKKKAAFAAWAAFAA-$NH_2$; | (SEQ ID NO: 3) |
| (d) | KKAFAAAAAFAAWAAFAKKKK-$NH_2$; | (SEQ ID NO: 4) |
| (e) | RRRAAFAAWAAFAARRR-$NH_2$; | (SEQ ID NO: 5) |
| (f) | KKAAAAFAAFAAWFAAFAAAAKKKK-$NH_2$; | (SEQ ID NO: 6) |
| (g) | KKATALVGAASLTAWVGLASAKKKK-$NH_2$. | (SEQ ID NO: 7) |
| (h) | KKAFAAAAAFAAXAAFAKKKK-$NH_2$; | (SEQ ID NO: 8) |
| (i) | KKKKKAAAFAAXAAFA-$NH_2$; | (SEQ ID NO: 9) |
| (j) | RRRAAAFAAXAAFARRR-$NH_2$; | (SEQ ID NO: 10) |
| (k) | KKAAAAFAAFAAXFAAFAAAAKKKK-$NH_2$; | (SEQ ID NO: 11) |
| (l) | KKATALVGAASLTAXVGLASAKKKK-$NH_2$; | (SEQ ID NO: 12) |
| (m) | KKKKKKAAAFAAAAAFAAWAAFAAA-$NH_2$; | (SEQ ID NO: 13) |
| (n) | KKKAAAFAAWAAFAKKK-$NH_2$; | (SEQ ID NO: 14) |
| (o) | RRRRRRAAFAAWAAFAA-$NH_2$; | (SEQ ID NO: 15) |
| (p) | KKKKKKAAAAFWAAAAF-$NH_2$; | (SEQ ID NO: 16) |
| (q) and | KKKKKKAAFAAFAAFAA-$NH_2$; | (SEQ ID NO: 17) |
| (r) | KKKKKKAAWAAWAAWAA-$NH_2$; | (SEQ ID NO: 18) | wherein X is any hydrophobic amino acid of hydropathy value greater than or equal to alanine.

In an aspect, the peptide is KKKKKKXXFXXWXXFXX-$NH_2$, wherein each X is independently A, L, G, or S (SEQ ID NO:1).

In another aspect, the peptide is KKKKKKAXFAXWM-FXA-NH$_2$, wherein each X is independently selected from A or L (SEQ ID NO:2).

In an aspect, the peptide is KKKKKKAAFAAWAAFAA-NH$_2$ (SEQ ID NO:3).

In an aspect, the amino acids in the peptide are D-amino acids, L-amino acids, or a combination thereof.

In an aspect, the peptide is a stapled peptide and in another aspect, the stapled peptide is a helix stapled peptide.

In another aspect, the antibiotic is selected from the group consisting of aminoglycosides, fluoroquinolones, carbapenem beta-lactam antibiotics, and combinations thereof.

In an aspect, the aminoglycosides are selected from tobramycin, streptomycin, neomycin, framycetin, paromomycin, ribostamycin, kanamycin, amikacin, arbekacin, bekanamycin, dibekacin, spectinomycin, hygromycin B, paromomycin sulfate, gentamicin, netilmicin, sisomicin, isepamicin, verdamicin, astromicin, and combinations thereof; the fluoroquinolones are selected from ciprofloxacin, cinoxacin, nalidixic acid, oxolinic acid, piromidic acid, pipemidic acid, rosoxacin, enoxacin, fleroxacin, lomefloxacin, nadifloxacin, norfloxacin, ofloxacin, pefloxacin, rufloxacin, balofloxacin, grepafloxacin, levofloxacin, pazufloxacin, sparfloxacin, temafloxacin, tosufloxacin, clinafloxacin, gatifloxacin, gemifloxacin, moxifloxacin, sitafloxacin, trovafloxacin, prulifloxacin, delafloxacin, JNJ-Q2, nemonoxacin, danofloxacin, difloxacin, enrofloxacin, ibafloxacin, marbofloxacin, orbifloxacin, sarafloxacin, and combinations thereof; and the carbapenem beta-lactam antibiotics are selected from meropenem, imipenem, ertapenem, doripenem, panipenem/betamipron, biapenem, razupenem, tebipenem, lenepenem, tomopenem, and combinations thereof.

In another aspect, the antibiotic is selected from tobramycin, ciprofloxacin, meropenem, and combinations thereof.

In an aspect, the infection is cystic fibrosis-related. In another aspect, the infection is caused by *Pseudomonas aeruginosa*. In another aspect, the infection is associated with a bacterial biofilm.

In an aspect, the method further comprises administering at least one additional antibiotic.

In another aspect, the method further comprises administering at least one additional peptide.

In another aspect, the method further comprises administering at least one additional therapeutic agent.

According to another aspect, there is provided a method for penetrating a bacterial biofilm, the method comprising administering a peptide comprising an amino acid sequence with a formula selected from the group consisting of:

(a) $B_{n1}$-Z;

(b) $B_{n1}$-Z-$B_{n2}$; and (c) Z-$B_{n1}$ wherein B is a basic amino acid residue;
n1 and n2 are 1 to 6; and
Z is a sequence of from about 7 to about 24 amino acid residues, said sequence having an average hydrophobicity value of at least 0.3 on the Liu-Deber scale.

In an aspect, the peptide is selected from the group consisting of (a) KKKKKKXXFXXWXXFXX-NH$_2$ (SEQ ID NO: 19)

(b) KKKKKKAXFAXWXAFXA-NH$_2$ (SEQ ID NO: 20)

(c) KKKKKKAAFAAWAAFAA-NH$_2$ (SEQ ID NO: 3)

(d) KKAFAAAAAFAAWAAFAKKKK-NH$_2$ (SEQ ID NO: 4)

(e) RRRAAFAAWAAFAARRR-NH$_2$ (SEQ ID NO: 5)

(f) KKAAAAFAAFAAWFAAFAAAAKKKK-NH$_2$ (SEQ ID NO: 6)

(g) KKATALVGAASLTAVVVGLASAKKKK-NH$_2$ (SEQ ID NO: 7)

(h) KKAFAAAAAFAAXAAFAKKKK-NH$_2$ (SEQ ID NO: 8)

(i) KKKKKAAAFAAXAAFA-NH$_2$ (SEQ ID NO: 9)

(j) RRRAAAFAAXAAFARRR-NH$_2$ (SEQ ID NO: 10)

(k) KKAAAAFAAFAAXFAAFAAAAKKKK-NH$_2$ (SEQ ID NO: 11)

(l) KKATALVGAASLTAXVGLASAKKKK-NH$_2$ (SEQ ID NO: 12)

(m) KKKKKKAAAFAAAAAFAAWAAFAAA-NH$_2$ (SEQ ID NO: 13)

(n) KKKAAAFAAWAAFAKKK-NH$_2$ (SEQ ID NO: 14)

(o) RRRRRRAAFAAWAAFAA-NH$_2$ (SEQ ID NO: 15)

(p) KKKKKKAAAAFWAAAAF-NH$_2$ (SEQ ID NO: 16)

(q) KKKKKKAAFAAFAAFAA-NH$_2$ (SEQ ID NO: 17)

and (r) KKKKKKAAWAAWAAWAA-NH$_2$ (SEQ ID NO: 18)

wherein X is any hydrophobic amino acid of hydropathy value greater than or equal to alanine.

In an aspect, the peptide is KKKKKKXXFXX-WXXFXX-NH$_2$, wherein each X is independently A, L, G, or S (SEQ ID NO:1), in synergistic combination with an antibiotic. In another aspect, the peptide is KKKKKKAX-FAXWXAFXA-NH$_2$, wherein each X is independently selected from A or L (SEQ ID NO:2).

In an aspect, the peptide is KKKKKKAAFAAWAAFAA-NH$_2$ (SEQ ID NO:3).

In an aspect, the amino acids in the peptide are D-amino acids, L-amino acids, or a combination thereof.

In an aspect, the peptide is a stapled peptide and in another aspect, the stapled peptide is a helix stapled peptide.

In another aspect, the peptide is administered in synergistic combination with an antibiotic.

In an aspect, the antibiotic is selected from the group consisting of aminoglycosides, fluoroquinolones, carbapenem beta-lactam antibiotics, and combinations thereof.

In an aspect, the aminoglycosides are selected from tobramycin, streptomycin, neomycin, framycetin, paromomycin, ribostamycin, kanamycin, amikacin, arbekacin, bekanamycin, dibekacin, spectinomycin, hygromycin B, paromomyqin sulfate, gentamicin, netilmicin, sisomicin, isepamicin, verdamicin, astromicin, and combinations thereof; the fluoroquinolones are selected from ciprofloxacin, cinoxacin, nalidixic acid, oxolinic acid, piromidic acid, pipemidic acid, rosoxacin, enoxacin, fleroxacin, lomefloxacin, nadifloxacin, norfloxacin, ofloxacin, pefloxacin, rufloxacin, balofloxacin, grepafloxacin, levofloxacin, pazufloxacin, sparfloxacin, temafloxacin, tosufloxacin, clinafloxacin, gatifloxacin, gemifloxacin, moxifloxacin, sitafloxacin, trovafloxacin, prulifloxacin, delafloxacin, JNJ-Q2, nemonoxacin, danofloxacin, difloxacin, enrofloxacin, ibafloxacin, marbofloxacin, orbifloxacin, sarafloxacin, and combinations thereof; and the carbapenem beta-lactam antibiotics are selected from meropenem, imipenem, ertapenem, doripenem, panipenem/betamipron, biapenem, razupenem, tebipenem, lenepenem, tomopenem, and combinations thereof.

In an aspect, the antibiotic is selected from tobramycin, ciprofloxacin, meropenem, and combinations thereof.

In an aspect, the bacterial biofilm is associated with sinusitis, a urinary tract infection, a middle-ear infection, dental plaque, gingivitis, contact lenses, endocarditis, cystic fibrosis, permanent indwelling devices such as joint prostheses, heart valves, catheters, and intrauterine devices, cutaneous wounds, or a surface that requires cleaning.

In an aspect, the method further comprises administering at least one additional antibiotic.

In an aspect, the method further comprises administering at least one additional peptide.

In an aspect, the method further comprises administering at least one additional therapeutic agent.

According to another aspect, there is provided a peptide KKKKKKXXFXXWXXFXX-NH$_2$ (SEQ ID NO:21), wherein each X is independently A or L.

In an aspect, the peptide is KKKKKKAAFAAWAAFAA-NH$_2$ (SEQ ID NO:3).

In an aspect, the amino acids in the peptide are D-amino acids, L-amino acids, or a combination thereof.

In an aspect, the peptide is a stapled peptide and in another aspect, the stapled peptide is a helix stapled peptide.

In another aspect, the peptide is for treating an infection.

In another aspect, the peptide is for penetrating a bacterial biofilm.

According to another aspect, there is provided a composition comprising a synergistic combination of an antibiotic and a peptide comprising an amino acid sequence with a formula selected from the group consisting of:

(a) $B_{n1}$-Z;

(b) $B_{n1}$-Z-$B_{n2}$; and (c) Z-$B_{n1}$ wherein B is a basic amino acid residue;
n1 and n2 are 1 to 6; and
Z is a sequence of from about 7 to about 24 amino acid residues, said sequence having an average hydrophobicity value of at least 0.3 on the Liu-Deber scale.

In an aspect, the peptide is selected from the group consisting of:

(a) KKKKKKXXFXXWXXFXX-NH$_2$; (SEQ ID NO: 19)

(b) KKKKKKAXFAXWXAFXA-NH$_2$; (SEQ ID NO: 20)

(c) KKKKKKAAFAAWAAFAA-NH$_2$; (SEQ ID NO: 3)

(d) KKAFAAAAAFAAWAAFAKKKK-NH$_2$; (SEQ ID NO: 4)

(e) RRRAAFAAWAAFAARRR-NH$_2$; (SEQ ID NO: 5)

(f) KKAAAAFAAFAAWFAAFAAAAKKKK-NH$_2$; (SEQ ID NO: 6)

(g) KKATALVGAASLTAWVGLASAKKKK-NH$_2$. (SEQ ID NO: 7)

(h) KKAFAAAAAFAAXAAFAKKKK-NH$_2$; (SEQ ID NO: 8)

(i) KKKKKAAAFAAXAAFA-NH$_2$; (SEQ ID NO: 9)

(j) RRRAAAFAAXAAFARRR-NH$_2$; (SEQ ID NO: 10)

(k) KKAAAAFAAFAAXFAAFAAAAKKKK-NH$_2$; (SEQ ID NO: 11)

(l) KKATALVGAASLTAXVGLASAKKKK-NH$_2$; (SEQ ID NO: 12)

(m) KKKKKKAAAFAAAAAFAAWAAFAAA-NH$_2$; (SEQ ID NO: 13)

(n) KKKAAAFAAWAAFAKKK-NH$_2$; (SEQ ID NO: 14)

(o) RRRRRRAAFAAWAAFAA-NH$_2$; (SEQ ID NO: 15)

(p) KKKKKKAAAAFWAAAAF-NH$_2$; (SEQ ID NO: 16)

(q) KKKKKKAAFAAFAAFAA-NH$_2$; (SEQ ID NO: 17)
and (r) KKKKKKAAWAAWAAWAA-NH$_2$; (SEQ ID NO: 18)

wherein X is any hydrophobic amino acid of hydropathy value greater than or equal to alanine.

In an aspect, the peptide is KKKKKKXXFXX-WXXFXX-NH$_2$, wherein each X is independently A, L, G, or S (SEQ ID NO:1), in synergistic combination with an antibiotic.

In another aspect, the peptide is KKKKKKAXFAXWX-AFXA-NH$_2$, wherein each X is independently selected from A or L (SEQ ID NO:2).

According to an aspect, the peptide is KKKKKKAAF-AAWAAFAA-NH$_2$ (SEQ ID NO:3).

In an aspect, the amino acids in the peptide are D-amino acids, L-amino acids, or a combination thereof.

In an aspect, the peptide is a stapled peptide and in another aspect, the stapled peptide is a helix stapled peptide.

According to another aspect, the antibiotic is selected from the group consisting of aminoglycosides, fluoroquinolones, carbapenem beta-lactam antibiotics, and combinations thereof.

In an aspect, the aminoglycosides are selected from tobramycin, streptomycin, neomycin, framycetin, paromomycin, ribostamycin, kanamycin, amikacin, arbekacin, bekanamycin, dibekacin, spectinomycin, hygromycin B, paromomycin sulfate, gentamicin, netilmicin, sisomicin, isepamicin, verdamicin, astromicin, and combinations thereof; the fluoroquinolones are selected from ciprofloxacin, cinoxacin, nalidixic acid, oxolinic acid, piromidic acid, pipemidic acid, rosoxacin, enoxacin, fleroxacin, lomefloxacin, nadifloxacin, norfloxacin, ofloxacin, pefloxacin, rufloxacin, balofloxacin, grepafloxacin, levofloxacin, pazufloxacin, sparfloxacin, temafloxacin, tosufloxacin, clinafloxacin, gatifloxacin, gemifloxacin, moxifloxacin, sitafloxacin, trovafloxacin, prulifloxacin, delafloxacin, JNJ-Q2, nemonoxacin, danofloxacin, difloxacin, enrofloxacin, ibafloxacin, marbofloxacin, orbifloxacin, sarafloxacin, and combinations thereof; and the carbapenem beta-lactam antibiotics are selected from meropenem, imipenem, ertapenem, doripenem, panipenem/betamipron, biapenem, razupenem, tebipenem, lenepenem, tomopenem, and combinations thereof.

In an aspect, the antibiotic is selected from tobramycin, ciprofloxacin, meropenem, and combinations thereof.

In an aspect, the composition is formulated as a toothpaste, mouthwash, topical skin product, contact lens cleaning or storage solution, parenteral or enteral composition, a cleaning solution, or a cleaning wipe.

In an aspect, the composition further comprises at least one additional antibiotic.

In an aspect, the composition further comprises at least one additional peptide.

In an aspect, the composition further comprises at least one additional therapeutic agent.

According to another aspect, there is provided a use of a peptide in synergistic combination with an antibiotic for treating an infection, wherein the peptide comprises an amino acid sequence with a formula selected from the group consisting of:

$$B_{n1}\text{-}Z; \quad (a)$$

$$B_{n1}\text{-}Z\text{-}B_{n2}; \text{ and} \quad (b)$$

$$Z\text{-}B_{n1} \quad (c)$$

wherein B is a basic amino acid residue;
n1 and n2 are 1 to 6; and
Z is a sequence of from about 7 to about 24 amino acid residues, said sequence having an average hydrophobicity value of at least 0.3 on the Liu-Deber scale.

In an aspect, the peptide is selected from the group consisting of:

| | | |
|---|---|---|
| (a) | KKKKKKXXFXXWXXFXX-NH$_2$; | (SEQ ID NO: 19) |
| (b) | KKKKKKAXFAXWXAFXA-NH$_2$; | (SEQ ID NO: 20) |
| (c) | KKKKKKAAFAAWAAFAA-NH$_2$; | (SEQ ID NO: 3) |
| (d) | KKAFAAAAAFAAWAAFAKKKK-NH$_2$; | (SEQ ID NO: 4) |
| (e) | RRRAAFAAWAAFAARRR-NH$_2$; | (SEQ ID NO: 5) |
| (f) | KKAAAAFAAFAAWFAAFAAAAKKKK-NH$_2$; | (SEQ ID NO: 6) |
| (g) | KKATALVGAASLTAWVGLASAKKKK-NH$_2$. | (SEQ ID NO: 7) |
| (h) | KKAFAAAAAFAAXAAFAKKKK-NH$_2$; | (SEQ ID NO: 8) |
| (i) | KKKKKAAAFAAXAAFA-NH$_2$; | (SEQ ID NO: 9) |
| (j) | RRRAAAFAAXAAFARRR-NH$_2$; | (SEQ ID NO: 10) |
| (k) | KKAAAAFAAFAAXFAAFAAAAKKKK-NH$_2$; | (SEQ ID NO: 11) |
| (l) | KKATALVGAASLTAXVGLASAKKKK-NH$_2$; | (SEQ ID NO: 12) |
| (m) | KKKKKKAAAFAAAAAFAAWAAFAAA-NH$_2$; | (SEQ ID NO: 13) |
| (n) | KKKAAAFAAWAAFAKKK-NH$_2$; | (SEQ ID NO: 14) |
| (o) | RRRRRRAAFAAWAAFAA-NH$_2$; | (SEQ ID NO: 15) |
| (p) | KKKKKKAAAAFWAAAAF-NH$_2$; | (SEQ ID NO: 16) |
| (q) and | KKKKKKAAFAAFAAFAA-NH$_2$; | (SEQ ID NO: 17) |
| (r) | KKKKKKAAWAAWAAWAA-NH$_2$. | (SEQ ID NO: 18) | wherein X is any hydrophobic amino acid of hydropathy value greater than or equal to alanine.

In an aspect, the peptide is KKKKKKXXFXX-WXXFXX-NH$_2$, wherein each X is independently A, L, G, or S (SEQ ID NO:1), in synergistic combination with an antibiotic.

In another aspect, the peptide is KKKKKKAXFAXWX-AFXA-NH$_2$, wherein each X is independently selected from A or L (SEQ ID NO:2).

In an aspect, the peptide is KKKKKKAAFAAWAAFAA-NH$_2$ (SEQ ID NO:3).

In an aspect, the amino acids in the peptide are D-amino acids, L-amino acids, or a combination thereof.

In an aspect, the peptide is a stapled peptide and in another aspect, the stapled peptide is a helix stapled peptide.

In another aspect, the antibiotic is selected from the group consisting of aminoglycosides, fluoroquinolones, carbapenem beta-lactam antibiotics, and combinations thereof.

In another aspect, the aminoglycosides are selected from tobramycin, streptomycin, neomycin, framycetin, paromomycin, ribostamycin, kanamycin, amikacin, arbekacin, bekanamycin, dibekacin, spectinomycin, hygromycin B, paromomycin sulfate, gentamicin, netilmicin, sisomicin, isepamicin, verdamicin, astromicin, and combinations thereof; the fluoroquinolones are selected from ciprofloxacin, cinoxacin, nalidixic acid, oxolinic acid, piromidic acid, pipemidic acid, rosoxacin, enoxacin, fleroxacin, lomefloxacin, nadifloxacin, norfloxacin, ofloxacin, pefloxacin, rufloxacin, balofloxacin, grepafloxacin, levofloxacin, pazufloxacin, sparfloxacin, temafloxacin, tosufloxacin, clinafloxacin, gatifloxacin, gemifloxacin, moxifloxacin, sitafloxacin, trovafloxacin, prulifloxacin, delafloxacin, JNJ-Q2, nemonoxacin, danofloxacin, difloxacin, enrofloxacin, ibafloxacin, marbofloxacin, orbifloxacin, sarafloxacin, and combinations thereof; and the carbapenem beta-lactam antibiotics are selected from meropenem, imipenem, ertapenem, doripenem, panipenem/betamipron, biapenem, razupenem, tebipenem, lenepenem, tomopenem, and combinations thereof.

In an aspect, the antibiotic is selected from tobramycin, ciprofloxacin, meropenem, and combinations thereof.

In another aspect, the infection is cystic fibrosis-related.

In another aspect, the infection is caused by *Pseudomonas aeruginosa*.

In an aspect, the infection is associated with a bacterial biofilm.

In an aspect, the use further comprises use of at least one additional antibiotic.

In an aspect, the use further comprises use of at least one additional peptide.

In an aspect, the use further comprises use of at least one additional therapeutic agent.

According to another aspect, there is provided a use of a peptide for penetrating a bacterial biofilm, wherein the peptide comprises an amino acid sequence with a formula selected from the group consisting of:

$B_{n1}$-Z;                                     (a)

$B_{n1}$-Z-$B_{n2}$; and                       (b)

Z-$B_{n1}$                                      (c)

wherein B is a basic amino acid residue;

n1 and n2 are 1 to 6; and

Z is a sequence of from about 7 to about 24 amino acid residues, said sequence having an average hydrophobicity value of at least 0.3 on the Liu-Deber scale.

In an aspect, the peptide is selected from the group consisting of (a) KKKKKKXXFXXWXXFXX-NH$_2$;   (SEQ ID NO: 19)

(b) KKKKKKAXFAXWXAFXA-NH$_2$;   (SEQ ID NO: 20)

(c) KKKKKKAAFAAWAAFAA-NH$_2$;   (SEQ ID NO: 3)

(d) KKAFAAAAAFAAWAAFAKKKK-NH$_2$;   (SEQ ID NO: 4)

(e) RRRAAFAAWAAFAARRR-NH$_2$;   (SEQ ID NO: 5)

(f) KKAAAAFAAFAAWFAAFAAAAKKKK-NH$_2$;   (SEQ ID NO: 6)

(g) KKATALVGAASLTAWVGLASAKKKK-NH$_2$.   (SEQ ID NO: 7)

(h) KKAFAAAAAFAAXAAFAKKKK-NH$_2$;   (SEQ ID NO: 8)

(i) KKKKKAAAFAAXAAFA-NH$_2$;   (SEQ ID NO: 9)

(j) RRRAAAFAAXAAFARRR-NH$_2$;   (SEQ ID NO: 10)

(k) KKAAAAFAAFAAXFAAFAAAAKKKK-NH$_2$;   (SEQ ID NO: 11)

(l) KKATALVGAASLTAXVGLASAKKKK-NH$_2$;   (SEQ ID NO: 12)

(m) KKKKKAAAFAAAAAFAAWAAFAAA-NH$_2$;   (SEQ ID NO: 13)

(n) KKKAAAFAAWAAFAKKK-NH$_2$;   (SEQ ID NO: 14)

(o) RRRRRAAFAAWAAFAA-NH$_2$;   (SEQ ID NO: 15)

(p) KKKKKKAAAAFWAAAAF-NH$_2$;   (SEQ ID NO: 16)

(q) KKKKKKAAFAAFAAFAA-NH$_2$;   (SEQ ID NO: 17)

and (r) KKKKKKAAWAAWAAWAA-NH$_2$;   (SEQ ID NO: 18)

wherein X is any hydrophobic amino acid of hydropathy value greater than or equal to alanine.

In another aspect, the peptide is KKKKKKXXFXX-WXXFXX-NH$_2$, wherein each X is independently A, L, G, or S (SEQ ID NO:1), in synergistic combination with an antibiotic.

In an aspect, the peptide is KKKKKKAXFAXWXAFXA-NH$_2$, wherein each X is independently selected from A or L (SEQ ID NO:2).

In another aspect, the peptide is KKKKKKAAF-AAWAAFAA-NH$_2$ (SEQ ID NO:3).

In an aspect, the amino acids in the peptide are D-amino acids, L-amino acids, or a combination thereof.

In an aspect, the peptide is a stapled peptide and in another aspect, the stapled peptide is a helix stapled peptide.

In an aspect, the peptide is for use in synergistic combination with an antibiotic.

In another aspect, the antibiotic is selected from the group consisting of aminoglycosides, fluoroquinolones, carbapenem beta-lactam antibiotics, and combinations thereof.

In another aspect, the aminoglycosides are selected from tobramycin, streptomycin, neomycin, framycetin, paromomycin, ribostamycin, kanamycin, amikacin, arbekacin, bekanamycin, dibekacin, spectinomycin, hygromycin B, paromomycin sulfate, gentamicin, netilmicin, sisomicin, isepamicin, verdamicin, astromicin, and combinations thereof; the fluoroquinolones are selected from ciprofloxacin, cinoxacin, nalidixic acid, oxolinic acid, piromidic acid, pipemidic acid, rosoxacin, enoxacin, fleroxacin, lomefloxacin, nadifloxacin, norfloxacin, ofloxacin, pefloxacin, rufloxacin, balofloxacin, grepafloxacin, levofloxacin, pazufloxacin, sparfloxacin, temafloxacin, tosufloxacin, clinafloxacin, gatifloxacin, gemifloxacin, moxifloxacin, sitafloxacin, trovafloxacin, prulifloxacin, delafloxacin, JNJ-Q2, nemonoxacin, danofloxacin, difloxacin, enrofloxacin, ibafloxacin, marbofloxacin, orbifloxacin, sarafloxacin, and combinations thereof; and the carbapenem beta-lactam antibiotics are selected from meropenem, imipenem, ertapenem, doripenem, panipenem/betamipron, biapenem, razupenem, tebipenem, lenepenem, tomopenem, and combinations thereof.

In an aspect, the antibiotic is selected from tobramycin, ciprofloxacin, meropenem, and combinations thereof.

In an aspect, the bacterial biofilm is associated with sinusitis, a urinary tract infection, a middle-ear infection, dental plaque, gingivitis, contact lenses, endocarditis, cystic fibrosis, permanent indwelling devices such as joint prostheses, heart valves, catheters, and intrauterine devices, cutaneous wounds, or a surface that requires cleaning.

In an aspect, the use further comprises use of at least one additional antibiotic.

In an aspect, the use further comprises use of at least one additional peptide.

In an aspect, the use further comprises use of at least one additional therapeutic agent.

According to another aspect, there is provided a method of treating a *P. aeruginosa* infection, the method comprising administering a composition comprising KKKKKKAAF-AAWAAFAA-NH$_2$ (SEQ ID NO:3) and an antibiotic selected from the group consisting of tobramycin, ciprofloxacin, and meropenem.

According to another aspect, there is provided a composition comprising KKKKKKAAFAAWAAFAA-NH$_2$ (SEQ ID NO:3) and an antibiotic selected from the group consisting of tobramycin, ciprofloxacin, and meropenem.

Other features and advantages of the present invention will become apparent from the following detailed description. It should be understood, however, that the detailed description and the specific examples while indicating aspects of the invention are given by way of illustration only, since various changes and modifications within the spirit and scope of the invention will become apparent to those skilled in the art from said detailed description.

DESCRIPTION OF THE FIGURES

The present invention will be further understood from the following description with reference to the Figures, in which.

DETAILED DESCRIPTION OF THE INVENTION

Figure 1:
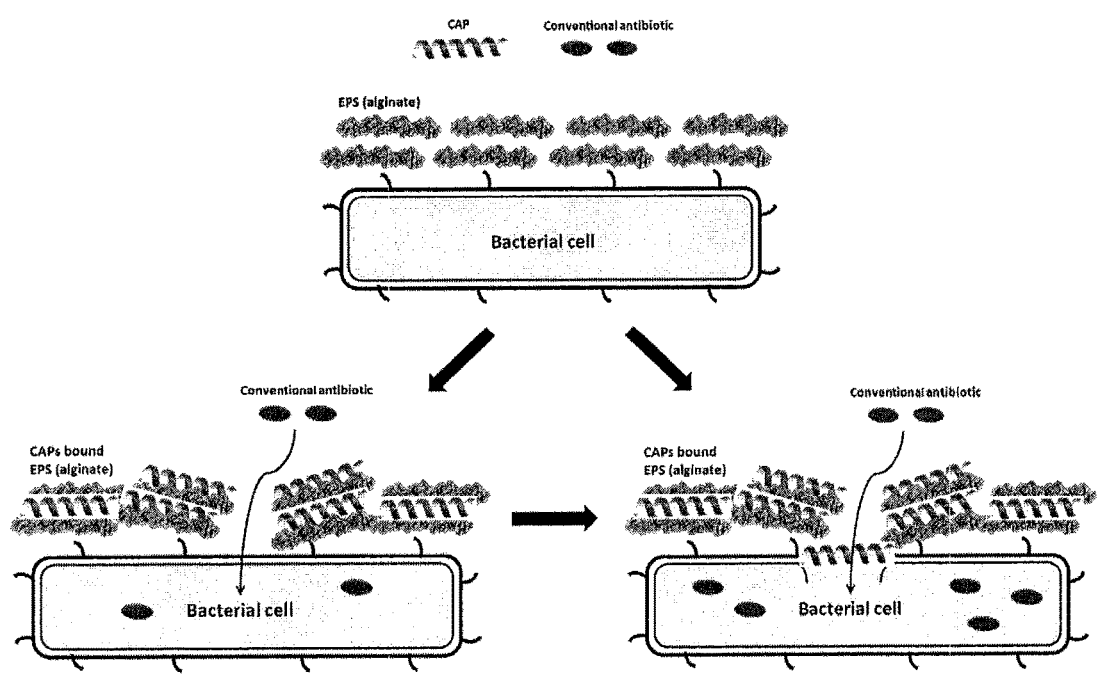
FIG. 1 is a schematic drawing of the proposed mechanism of action of the peptides described herein.

The present invention is directed to methods of treating infections through use of cationic antimicrobial peptides, such as KKKKKKXXFXXWXXFXX-NH$_2$ (SEQ ID NO:1), wherein each X is independently A, L, G, or S. For example, the peptide in an aspect is KKKKKKAXFAXWX-AFXA-NH$_2$, (SEQ ID NO:2) wherein each X is independently selected from A or L, such as KKKKKKAAF-AAWAAFAA-NH$_2$ (SEQ ID NO:3).

In aspects, the methods involve the use of a cationic antimicrobial peptide in synergistic combination with an antibiotic. The present invention is also directed to methods of penetrating bacterial biofilms through use of the cationic antimicrobial peptides alone or in synergistic combination with an antibiotic. Unexpectedly, the peptides described herein are able to penetrate bacterial biofilms. This not only allows efficacious treatment with the antimicrobial peptides, but also improves penetration by other antibiotics, thereby providing a synergistic treatment of infectious disease.

"Variants" of the sequences described herein are biologically active sequences that have a nucleotide or amino acid sequence that differs from the parent sequence (or the complement thereof), by virtue of an insertion, deletion, modification and/or substitution of one or more nucleotides or amino acids within the native sequence. Such variants generally have less than 100% sequence identity with the parent sequence or its complement. Ordinarily, however, a biologically active variant will have a nucleotide or amino acid sequence with at least about 70% sequence identity with the sequence or complement of a corresponding naturally occurring sequence, typically at least about 75%, more typically at least about 80%, even more typically at least about 85%, even more typically at least about 90%, and even more typically of at least about 95%, 96%, 97%, 98%, or 99% sequence identity. The variants include nucleotide or amino acid fragments of any length that retain a biological activity of the corresponding parent sequence. Variants also include sequences wherein one or more nucleotides or amino acids are added at the 5' or 3' end of, or within, the parent sequence or its complement. Variants also include sequences where one or more nucleotides or amino acids are deleted and optionally substituted by one or more different nucleotides or amino acids.

"Percent sequence identity" is defined herein as the percentage of nucleotides or amino acid residues in the candidate sequence that are identical with the nucleotides or residues in the sequence of interest after aligning the sequences and introducing gaps, if necessary, to achieve the maximum percent sequence identity, and not considering any conservative substitutions as part of the sequence identity. None of 5', 3', or internal extensions, deletions or insertions into the candidate sequence shall be construed as affecting sequence identity or homology. Methods and computer programs for the alignment are well known in the art, such as "BLAST".

"Active" or "activity" for the purposes herein refers to a biological activity of the parent cationic antimicrobial peptide sequence, wherein "biological" activity refers to a biological function caused by the parent sequence. Thus, "biologically active" or "biological activity" when used in conjunction with "cationic antimicrobial peptides" refers to a nucleotide or amino acid sequence that exhibits or shares an effector function of the parent cationic antimicrobial peptide sequence. For example, the cationic antimicrobial peptides described herein have the biological activity of preventing, inhibiting, or treating an infection and/or of penetrating a bacterial biofilm.

"Biologically active" or "biological activity" when used in conjunction with variant sequences means that the variant sequences exhibit or share an effector function of the parent sequence. The biological activity of the variant sequence may be increased, decreased, or at the same level as compared with the parent sequence.

The terms "inhibit" or "inhibitory" mean that a function or activity of an infectious organism is decreased, limited, blocked, or neutralized. These terms encompass a complete or partial inhibition in function or activity.

"Isolated" refers to a molecule that has been purified from its source or has been prepared by recombinant or synthetic methods and purified. Purified nucleotides are substantially free of other nucleotides or bases.

"Substantially free" herein means less than about 5%, typically less than about 2%, more typically less than about 1%, even more typically less than about 0.5%, most typically less than about 0.1% contamination with other source nucleotides or amino acids. "Essentially pure" means a composition comprising at least about 90% by weight of the nucleotide or peptide, based on total weight of the composition, typically at least about 95% by weight, more typically at least about 90% by weight, even more typically at least about 95% by weight, and even more typically at least about 99% by weight of nucleotide or peptide, based on total weight of the composition.

As used herein, "treatment" or "therapy" is an approach for obtaining beneficial or desired clinical results. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" and "therapy" can also mean prolonging survival as compared to expected survival if not receiving treatment or therapy. Thus, "treatment" or "therapy" is an intervention performed with the intention of altering the pathology of a disorder. Specifically, the treatment or therapy may directly prevent, slow down or otherwise decrease the pathology of an infectious disease, or may render the subject more susceptible to treatment or therapy by other therapeutic agents.

The terms "therapeutically effective amount", "effective amount" or "sufficient amount" mean a quantity sufficient, when administered to a subject, including a mammal, for example a human, to achieve a desired result, for example an amount effective to treat an infectious disease and/or penetrate a bacterial biofilm. Effective amounts of the agents described herein may vary according to factors such as the disease state, age, sex, and weight of the subject. Dosage or treatment regimes may be adjusted to provide the optimum therapeutic response, as is understood by a skilled person.

Moreover, a treatment regime of a subject with a therapeutically effective amount may consist of a single administration, or alternatively comprise a series of applications. The length of the treatment period depends on a variety of factors, such as the severity of the disease, the age of the subject, the concentration of the agent, the responsiveness of the patient to the agent, or a combination thereof. It will also be appreciated that the effective dosage of the agent used for the treatment may increase or decrease over the course of a particular treatment regime. Changes in dosage may result and become apparent by standard diagnostic assays known in the art. The agents of the present invention may, in aspects, be administered before, during or after treatment with conventional therapies for the disease or disorder in question, such as an infection associated with or without a bacterial biofilm.

The term "subject" as used herein refers to any member of the animal kingdom, typically a mammal. The term "mammal" refers to any animal classified as a mammal, including humans, other higher primates, domestic and farm animals, and zoo, sports, or pet animals, such as dogs, cats, cattle, horses, sheep, pigs, goats, rabbits, etc. Typically, the mammal is human.

Administration "in combination with" one or more further therapeutic agents includes simultaneous (concurrent) and consecutive administration in any order.

"Carriers" as used herein include pharmaceutically acceptable carriers, excipients, or stabilizers that are non-toxic to the cell or mammal being exposed thereto at the dosages and concentrations employed. Often the pharmaceutically acceptable carrier is an aqueous pH buffered solution. Examples of pharmacologically acceptable carriers include buffers such as phosphate, citrate, and other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, and dextrins; chelating agents such as EDTA; sugar alcohols such as mannitol and sorbitol; salt-forming counterions such as sodium; and/or nonionic surfactants such as TWEEN™, polyethylene glycol (PEG), and PLURONICS™.

A "liposome" is a small vesicle composed of various types of lipids, phospholipids and/or surfactant that is useful for delivery of a drug to a subject, such as a mammal. The components of the liposome are commonly arranged in a bilayer formation, similar to the lipid arrangement of biological membranes.

"Penetration of a bacterial biofilm" refers to the ability of the peptides described herein to bind to EPS in the biofilm and/or pass through the EPS into bacterial cells.

In understanding the scope of the present application, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. Anything referred to in this document as "comprising," "having," or "including" any specific components should also be considered to have been separately described as "consisting of" or "consisting essentially of" those same components. The terms "a" or "an" are used to include one or more than one and the term "or" is used to refer to a nonexclusive "or" unless otherwise indicated. Finally, terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

The peptides described herein interact with bacterial cell walls and thereby find use in treatment of bacterial infections and in penetrating bacterial biofilms. Combinations of such peptides may also be employed and may act together synergistically or additively. Advantageously, the peptides described herein are shown to act synergistically with certain conventional antibiotics and also show activity against various forms and strains of P. aeruginosa. Further, one of the important advantages of the peptides described herein over conventional antibiotics is their ability to cause rapid killing via physical mechanisms and preclude the development of resistance. The peptides described herein, such as KKKKKKAAFAAWAAFAA-NH$_2$ (SEQ ID NO:3), are effective against Gram-positive and Gram-negative bacteria and yeast.

Typically, the agent is a cationic antimicrobial peptide as described in CA 2,451,310 or in Yin et al. (both of which are incorporated by reference herein in their entirety). For example, the cationic antimicrobial peptide may have an amino acid sequence having a formula selected from the group consisting of:

$$B_{n1}\text{-}Z; \quad (a)$$

$$B_{n1}\text{-}Z\text{-}B_{n2}; \text{ and} \quad (b)$$

$$Z\text{-}B_{n1} \quad (c)$$

wherein B is a basic amino acid residue;
n1 and n2 are 1 to 6; and
Z is a sequence of about 7 to about 24 amino acid residues, said sequence having an average hydrophobicity value of at least 0.3 on the Liu-Deber scale, for the treatment or prevention of a microbial infection.

The Liu-Deber scale provides a hydrophobicity value for each guest residue, which is determined from the retention time of the corresponding X peptide as found by reverse-phase high-performance liquid chromatography (RP-HPLC) (see Liu and Deber; Review Guidelines for membrane protein engineering derived from de novo designed model peptides; Biopolymers; 1998; 47(1):41-62, which is incorporated by reference herein in its entirety).

Basic amino acid residues include histidine, lysine, and arginine.

Specific examples of such cationic antimicrobial peptides include the following:

(a) KKKKKKXXFXXWXXFXX-NH$_2$, wherein each X is independently A, L, G, or S (SEQ ID NO:1);

(b) KKKKKKAXFAXWXAFXA-NH$_2$, wherein each X is independently selected from A or L (SEQ ID NO:2);

(c) KKKKKKAAFAAWAAFAA-NH$_2$; (SEQ ID NO: 3)

(d) KKAFAAAAAFAAWAAFAKKKK-NH$_2$; (SEQ ID NO: 4)

(e) RRRAAFAAWAAFAARRR-NH$_2$; (SEQ ID NO: 5)

(f) KKAAAAFAAFAAWFAAFAAAAKKKK-NH$_2$; (SEQ ID NO: 6)

(g) KKATALVGAASLTAVVVGLASAKKKK-NH$_2$. (SEQ ID NO: 7)

(h) KKAFAAAAAFAAXAAFAKKKK-NH$_2$; (SEQ ID NO: 8)

(i) KKKKKAAFAAXAAFA-NH$_2$ (SEQ ID NO: 9)

(j) RRRAAAFAAXAAFARRR-NH$_2$; (SEQ ID NO: 10)

(k) KKAAAAFAAFAAXFAAFAAAAKKKK-NH$_2$; (SEQ ID NO: 11)

(l) KKATALVGAASLTAXVGLASAKKKK-NH$_2$; (SEQ ID NO: 12)

(m) KKKKKKAAAFAAAAAFAAWAAFAAA-NH$_2$; (SEQ ID NO: 13)

(n) KKKAAAFAAWAAFAKKK-NH$_2$; (SEQ ID NO: 14)

(o) RRRRRRAAFAAWAAFAA-NH$_2$; (SEQ ID NO: 15)

(p) KKKKKKAAAAFWAAAAF-NH$_2$; (SEQ ID NO: 16)

(q) and KKKKKKAAFAAFAAFAA-NH$_2$; (SEQ ID NO: 17)

(r) KKKKKKAAWAAWAAWAA-NH$_2$; (SEQ ID NO: 18)

wherein X is any hydrophobic amino acid of hydropathy value greater than or equal to alanine.

Typically, the sequence of the cationic antimicrobial peptide is KKKKKKXXFXXWXXFXX-NH$_2$ (SEQ ID NO:1), wherein each X is independently A, L, G, or S and, more typically, the sequence of the cationic antimicrobial peptide is KKKKKKAXFAXWXAFXA-NH$_2$, wherein each X is independently selected from A or L (SEQ ID NO:2). Even more typically, the sequence is KKKKKKAAFAAWAAFAA-NH$_2$ (SEQ ID NO:3).

Generally, the sequences have primarily alanine residues and fewer than three leucine residues in the "X" positions in order to avoid significant hemolysis. Such sequences, having mostly alanine residues in the "X" positions are better suited to delivery in vivo as they are less likely to cause significant haemolytic damage to red blood cells.

The peptides described herein may have all D-amino acids, all L-amino acids, or a combination of D- and L-amino acids. The D-amino acid form of KKKKKKAAF-AAWAAFAA-NH$_2$ (SEQ ID NO:3) was tested in the examples described below, however, the L-amino acid form or a peptide having a combination of D- and L-amino acids would also be expected to work in a similar way. The peptides described herein are not acting like typical ligands by binding to a receptor, in which actual peptide optical form (L- or D- of any given amino acid) would be particularly important. Instead, the peptides are interacting with the bacterial cell wall in a receptor-independent manner.

In a typical aspect, the cationic antimicrobial peptide is suitable for delivery in vivo, e.g., to an organism. In another aspect, the cationic antimicrobial peptide is suitable for delivery in vitro, e.g., to a cell culture or a cell suspension. The cationic antimicrobial peptide can include a ligand that is selected to improve stability, distribution or cellular uptake of the agent. For example, the ligand can be a lipophilic moiety, e.g., cholesterol, which enhances entry of the cationic antimicrobial peptide into a cell.

The peptides described herein may be formulated into compositions, which may further comprise one or more pharmaceutically acceptable excipients, carriers, buffers, stabilizers, adjuvants, or mixtures thereof.

Therapeutic compositions of the peptides are prepared for storage by mixing the desired peptide having the appropriate degree of purity with optional pharmaceutically acceptable carriers, excipients, and/or stabilizers (Remington's Pharmaceutical Sciences, 16th edition, Osol, A. ed. (1980), incorporated herein by reference in its entirety), in the form of lyophilized formulations or aqueous solutions. Acceptable carriers, excipients, or stabilizers are nontoxic to recipients at the dosages and concentrations employed.

Examples of such carriers include ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts, or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances, and polyethylene glycol. Carriers for topical or gel-based forms of the agents include polysaccharides such as sodium carboxymethylcellulose or methylcellulose, polyvinylpyrrolidone, polyacrylates, polyoxyethylene-polyoxypropylene-block polymers, polyethylene glycol, and wood wax alcohols. For all administrations, conventional depot forms may be used. Such forms include, for example, microcapsules, nano-capsules, liposomes, plasters, inhalation forms, nose sprays, sublingual tablets, and sustained-release preparations.

The peptides will typically be formulated in such vehicles at a concentration of about 0.01 mg/ml to about 100 mg/ml, such as about 0.1 to about 1 mg/ml.

Peptides to be used for in vivo administration are generally sterile. This is readily accomplished, for example, by filtration through sterile filtration membranes, prior to or following lyophilization and reconstitution. The peptides ordinarily will be stored in lyophilized form or in solution if administered systemically. If in lyophilized form, the peptides are typically formulated in combination with other ingredients for reconstitution with an appropriate diluent at the time of use. An example of a liquid formulation of the agents described herein is a sterile, clear, colorless unpreserved solution filled in a single-dose vial for subcutaneous injection. Preserved pharmaceutical compositions suitable for repeated use may contain, for example, depending mainly on the indication and type of peptide: the peptide; a buffer capable of maintaining the pH in a range of maximum stability of the agent in solution, typically about 4-8; a detergent/surfactant primarily to stabilize the agent against agitation-induced aggregation; an isotonifier; a preservative selected from the group of phenol, benzyl alcohol and a benzethonium halide, e.g., chloride; and water.

If the detergent employed is non-ionic, it may, for example, comprise polysorbates (e.g., POLYSORBATE™ (TWEEN™) 20, 80, etc.) or poloxamers (e.g., POLOXAMER™ 188). The use of non-ionic surfactants permits the formulation to be exposed to shear surface stresses without causing denaturation of the agent. Further, such surfactant-containing formulations may be employed in aerosol devices such as those used in a pulmonary dosing, and needleless jet injector guns (see, e.g., EP 257,956, incorporated herein by reference in its entirety).

An isotonifier may be present to ensure isotonicity of a liquid composition of the agents described herein, and includes polyhydric sugar alcohols, typically trihydric or higher sugar alcohols, such as glycerin, erythritol, arabitol, xylitol, sorbitol, and mannitol. These sugar alcohols can be used alone or in combination. Alternatively, sodium chloride or other appropriate inorganic salts may be used to render the solutions isotonic.

The buffer may, for example, be an acetate, citrate, succinate, or phosphate buffer depending on the pH desired. The pH of one type of liquid formulation of this invention is buffered in the range of about 4 to 8, typically about physiological pH.

The preservatives phenol, benzyl alcohol and benzethonium halides, e.g., chloride, are known antimicrobial agents that may be employed.

Therapeutic compositions described herein generally are placed into a container having a sterile access port, for example, an intravenous solution bag or vial having a stopper pierceable by a hypodermic injection needle. The formulations are typically administered as repeated intravenous (i.v.), subcutaneous (s.c.), or intramuscular (i.m.) injections, or as aerosol formulations suitable for intranasal or intrapulmonary delivery (for intrapulmonary delivery see, e.g., EP 257,956, incorporated herein by reference in its entirety).

An article of manufacture, such as a kit containing an agent useful for the treatment of the disorders described herein, comprises at least a container and a label. Suitable containers include, for example, bottles, vials, syringes, and test tubes. The containers may be formed from a variety of materials such as glass or plastic. The container holds a composition that is effective for diagnosing or treating the condition and may have a sterile access port (for example, the container may be an intravenous solution bag or a vial having a stopper pierceable by a hypodermic injection needle). The active agent in the composition is an agent described herein. The label on, or associated with, the container indicates that the composition is used for treating the condition of choice. The article of manufacture may further comprise a second container comprising a pharmaceutically-acceptable buffer, such as phosphate-buffered saline, Ringer's solution, or dextrose solution. It may further include other materials desirable from a commercial and user standpoint, including other buffers, diluents, filters, needles, syringes, and package inserts with instructions for use. The article of manufacture may also comprise a second or third container with another active pharmaceutical agent as described herein.

The peptides described herein can also be administered in the form of sustained-released preparations. Suitable examples of sustained-release preparations include semipermeable matrices of solid hydrophobic polymers containing the agent, which matrices are in the form of shaped articles, e.g., films or microcapsules. Examples of sustained-release matrices include polyesters, hydrogels (e.g., poly(2-hydroxyethyl-methacrylate) as described by Langer et al., J. Biomed. Mater. Res. 15:167-277 (1981) and Langer, Chem. Tech. 12:98-105 (1982) or poly(vinylalcohol)), polylactides (U.S. Pat. No. 3,773,919, EP 58,481), copolymers of L-glutamic acid and gamma ethyl-L-glutamate (Sidman et al., Biopolymers 22:547-556 (1983)), non-degradable ethylene-vinyl acetate (Langer et al., supra), degradable lactic acid-glycolic acid copolymers such as the Lupron Depot™ (injectable microspheres composed of lactic acid-glycolic acid copolymer and leuprolide acetate), and poly-D-(-)-3-hydroxybutyric acid (EP 133,988). Each of these references is incorporated herein by reference in its entirety.

Sustained-release compositions also include liposomally entrapped peptides. Liposomes containing the peptides described herein are prepared by methods known per se: DE 3,218,121; Epstein et al., Proc. Natl. Acad. Sci. USA 82:3688-3692 (1985); Hwang et al., Proc. Natl. Acad. Sci. USA 77:4030-4034 (1980); EP 52,322; EP 36,676; EP 88,046; EP 143,949; EP 142,641; Japanese patent application 83-118008; U.S. Pat. Nos. 4,485,045 and 4,544,545; and EP 102,324, each of which is incorporated herein by reference. Ordinarily the liposomes are of the small (about 200-800 Angstroms) unilamellar type in which the lipid content is greater than about 30 mol. % cholesterol, the selected proportion being adjusted for the optimal therapy.

Other similar delivery methods, such as via nanocapsules, microparticles, microspheres, nanoparticles, lipid particles, vesicles, and the like are contemplated. The peptides may be formulated for delivery either encapsulated in a lipid particle, a liposome, a vesicle, a nanosphere, or a nanoparticle for example, and may further include a targeting molecule exposed to aid in site-specific delivery of the agent.

The formation and use of liposomes is generally known to those of skill in the art (see for example, Couvreur et al., FEBS Lett. 1977 Dec. 15; 84(2):323-6; Couvreur, Crit Rev Ther Drug Carrier Syst. 1988; 5(1):1-20; Lasic, Trends Biotechnol. 1998 July; 16(7):307-21; Gabizon & Papahadjopoulos, Proc Natl Acad Sci USA. 1988 September; 85(18):6949-53; Allen and Chonn, FEBS Lett. 1987 Oct. 19; 223(1):42-6; U.S. Pat. No. 5,741,516, which are incorporated by reference herein in their entirety).

Liposomes bear resemblance to cellular membranes and are contemplated for use in connection with the present invention as carriers for the peptides. They are widely suitable as both water- and lipid-soluble substances can be entrapped, i.e. in the aqueous spaces and within the bilayer itself, respectively.

The therapeutically effective dose of the peptides will, of course, vary depending on such factors as the specific peptide in question, the pathological condition to be treated (including prevention), the method of administration, any co-therapy involved, the subject's age, weight, general medical condition, medical history, etc., and its determination is well within the skill of a practicing physician. Accordingly, it may be necessary for the clinician to titer the dosage and modify the route of administration as required to obtain the maximal therapeutic effect. The clinician will administer the agent until a dosage is reached that achieves the desired effect for treatment of the condition in question.

For example, if the objective is the treatment of an infectious disease, the amount would be, in one aspect, one that improves the condition.

With the above guidelines, the effective dose generally is within the range of from about 0.01 μg/kg to about 100 mg/kg, 1 to about 50 mg/kg, more typically from about 1 to about 25 mg/kg, and most typically from about 1 to about 5 mg/kg.

For non-oral use, agents may be administered in the form of an injection at about 0.01 μg/kg to about 100 mg/kg, 1 to 50 mg, typically about 1 to about 25 mg, most typically about 1 to about 5 mg, per kg body weight, 1 to 2 times daily by intravenous injection. It should be appreciated that endotoxin contamination should be kept minimally at a safe level, for example, less than about 0.5 ng/mg protein. Moreover, for human administration, the formulations generally meet sterility, pyrogenicity, general safety, and purity as required by the FDA Office and Biologics standards.

Certain factors may influence the dosage required to effectively treat a subject, including but not limited to the severity of the disease or disorder, previous treatments, the general health and/or age of the subject, and other diseases present. It will also be appreciated that the effective dosage of the peptide used for treatment may increase or decrease over the course of a particular treatment. Changes in dosage may result and become apparent from the results of diagnostic assays. For example, the subject can be monitored after administering a peptide described herein. Based on information from the monitoring, an additional amount of the peptide can be administered.

Dosing is dependent on severity and responsiveness of the disease condition to be treated, with the course of treatment lasting from several days to several months, or until a cure is effected or a diminution of disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual compounds, and can generally be estimated based on $EC_{50}$s found to be effective in in vitro and in vivo animal models.

Dosage levels on the order of about 0.01 μg/kg to 100 mg/kg of body weight per administration are useful in the treatment of a disease. One skilled in the art can also readily determine an appropriate dosage regimen for administering the disclosed to a given subject. For example, a peptide described herein can be administered to the subject once, e.g., as a single injection. Alternatively, the agent can be administered once or twice daily to a subject for a period of from about three to about twenty-eight days, or from about seven to about ten days.

Thus, the agent can be administered at a unit dose less than about 100 mg per kg of bodyweight, or less than about 90, 80, 70, 60, 50, 40, 30, 20, 10, 5, 2, 1, 0.5, 0.1, 0.05, 0.01, 0.005, 0.001, or 0.0005 mg per kg of bodyweight, and less than 200 nmol of agent per kg of bodyweight, or less than 1500, 750, 300, 150, 75, 15, 7.5, 1.5, 0.75, 0.15, 0.075, 0.015, 0.0075, 0.0015, 0.00075, 0.00015 nmol of agent per kg of bodyweight.

Delivery of a peptide described herein directly to an organ (e.g., directly to the lungs) can be at a dosage on the order of about 0.00001 mg to about 3 mg per organ, or typically about 0.0001-0.001 mg per organ, about 0.03-3.0 mg per organ, about 0.1-3.0 mg per organ or about 0.3-3.0 mg per organ.

Where a dosage regimen comprises multiple administrations, it is understood that the effective amount of peptide administered to the subject can include the total amount of peptide administered over the entire dosage regimen. One skilled in the art will appreciate that the exact individual dosages may be adjusted somewhat depending on a variety of factors, including the specific agent being administered, the time of administration, the route of administration, the nature of the formulation, the rate of excretion, the particular disorder being treated, the severity of the disorder, the pharmacodynamics of the peptide, and the age, sex, weight, and general health of the patient. Wide variations in the necessary dosage level are to be expected in view of the differing efficiencies of the various routes of administration. For instance, oral administration would require higher dosage levels than administration by intravenous injection. Variations in these dosage levels can be adjusted using standard empirical routines of optimization, which are well-known in the art. The precise therapeutically effective dosage levels and patterns are typically determined by the attending physician in consideration of the above-identified factors. In one aspect, the unit dose is administered less frequently than once a day, e.g., less than every 2, 4, 8 or 30 days. In another aspect, the unit dose is not administered with a frequency (e.g., not a regular frequency). For example, the unit dose may be administered a single time.

In some aspects, a subject is administered an initial dose, and one or more maintenance doses of a peptide described herein. The maintenance dose or doses are generally lower than the initial dose, e.g., one-half less of the initial dose. A maintenance regimen can include treating the subject with a dose or doses ranging from 0.01 μg to 100 mg/kg of body weight per day, e.g., 70, 60, 50, 40, 30, 20, 10, 5, 2, 1, 0.5, 0.1, 0.05, 0.01, 0.005, 0.001, or 0.0005 mg per kg of bodyweight per day. The maintenance doses are typically administered no more than once every 5, 10, or 30 days. Further, the treatment regimen may last for a period of time, which will vary depending upon the nature of the particular disease, its severity and the overall condition of the patient. In typical aspects, the dosage may be delivered no more than once per day, e.g., no more than once per 24, 36, 48, or more hours, e.g., no more than once every 5 or 8 days. Following treatment, the patient can be monitored for changes in his condition and for alleviation of the symptoms of the disease state. The dosage of the peptide may either be increased in the event the patient does not respond significantly to current dosage levels, or the dose may be decreased if an alleviation of the symptoms of the disease state is observed, if the disease state has been ablated, or if undesired side-effects are observed.

The effective dose can be administered in a single dose or in two or more doses, as desired or considered appropriate under the specific circumstances. If desired to facilitate repeated or frequent infusions, implantation of a delivery device, e.g., a pump, semi-permanent stent (e.g., intravenous, intraperitoneal, intracisternal or intracapsular), or reservoir may be advisable. Following successful treatment, it may be desirable to have the patient undergo maintenance therapy to prevent the recurrence of the disease state, wherein the peptide of the invention is administered in maintenance doses, ranging from 0.01 μg to 100 g per kg of body weight.

In addition to treating pre-existing diseases or disorders, the peptide described herein can be administered prophylactically in order to prevent or slow the onset of a particular disease or disorder. In prophylactic applications, a peptide is administered to a patient susceptible to or otherwise at risk of a particular disorder, such as a communicable infectious disease.

The route of administration is in accord with known methods, e.g., by injection or infusion by intravenous, intramuscular, intracerebral, intraperitoneal, intracerebrospinal, subcutaneous, intraocular, intraarticular, intrasynovial, intrathecal, oral, topical, or inhalation routes, or by sustained-release systems.

The effectiveness of a peptide in preventing or treating the disorder in question may be improved by administering the peptide serially or in combination with another pharmacological agent that is effective for analogous purposes, either in the same composition or as separate compositions.

For example, the peptides described herein may be combined with antibiotic therapies and may act synergistically or additively with such other therapies. Examples of such antibiotic therapies include aminoglycosides, such as tobramycin, streptomycin, neomycin, framycetin, paromomycin, ribostamycin, kanamycin, amikacin, arbekacin, bekanamycin, dibekacin, spectinomycin, hygromycin B, paromomycin sulfate, gentamicin, netilmicin, sisomicin, isepamicin, verdamicin, and astromicin; fluoroquinolones, such as ciprofloxacin, cinoxacin, nalidixic acid, oxolinic acid, piromidic acid, pipemidic acid, rosoxacin, enoxacin, fleroxacin, lomefloxacin, nadifloxacin, norfloxacin, ofloxacin, pefloxacin, rufloxacin, balofloxacin, grepafloxacin, levofloxacin, pazufloxacin, sparfloxacin, temafloxacin, tosufloxacin, clinafloxacin, gatifloxacin, gemifloxacin, moxifloxacin, sitafloxacin, trovafloxacin, prulifloxacin, delafloxacin, JNJ-Q2, nemonoxacin, danofloxacin, difloxacin, enrofloxacin, ibafloxacin, marbofloxacin, orbifloxacin, and sarafloxacin; and carbapenem beta-lactam antibiotics such as meropenem, imipenem, ertapenem, doripenem, panipenem/betamipron, biapenem, razupenem, tebipenem, lenepenem, and tomopenem. In an aspect, the antibiotic is tobramycin, ciprofloxacin, or meropenem.

The effective amounts of the therapeutic agents administered in combination with the agents described herein will be at the physician's or veterinarian's discretion. Dosage administration and adjustment is done to achieve maximal management of the conditions to be treated. The dose will additionally depend on such factors as the type of the therapeutic agent to be used and the specific patient being treated. Typically, the amount employed will be the same dose as that used, if the given therapeutic agent is administered without the agents described herein.

The agents described herein can be formulated in combination with another agent, such as an agent that stabilizes a peptide. Still other agents include chelators, e.g., EDTA (e.g., to remove divalent cations such as $Mg^{2+}$) and salts.

In an aspect, the peptides described herein find use in treating an infectious disease, such as a cystic-fibrosis related infection or an infection caused by *Pseudomonas aeruginosa*. In an alternative or complementary aspect, the peptides described herein find use in penetrating bacterial biofilms. Infectious processes in which biofilms have been implicated include common problems such as sinusitis, urinary tract infections, middle-ear infections, formation of dental plaque, gingivitis, coating contact lenses, and less common but more lethal processes such as endocarditis, infections in cystic fibrosis, and infections of permanent indwelling devices such as joint prostheses, heart valves, catheters, and intrauterine devices. Bacterial biofilms may also impair cutaneous wound healing and reduce topical antibacterial efficiency in healing or treating infected skin wounds. The peptides described herein are expected to find use in treatment or prevention of any conditions in which biofilms are implicated.

Thus, one or more peptides described herein, optionally together with one or more antibiotics, could be incorporated into toothpastes or mouthwashes, into topical creams, gels, pastes, or ointments, into the surface coatings of indwelling devices, into contact lens storage or cleaning solutions, or into enteral or parenteral formulations, for example.

The peptides described herein would be expected to be particularly beneficial as topical formulations for treatment of skin infections, as they would not be subject to the metabolism that would occur following enteral or parenteral administration.

Furthermore, biofilms may be found on inert surfaces and, therefore, the peptides described herein can be incorporated into cleaning solutions or wipes, for example, for cleaning tables, hospital surfaces, medical devices, and so on. The peptides described herein find use as adjuvants to standard biocides for washing or disinfecting surfaces.

The peptides described herein may also be used as a component of personalized medicine. As treatment of infectious diseases varies depending upon an individual's susceptibility or resistance to various antibiotics, the peptides described herein may be used to enhance the activity of conventional antibiotics or to resensitize patients to antibiotics to which they have grown resistant.

As antibiotic cocktails are generally not significantly better than individual antibiotics for the treatment of resistant infections, the peptides described herein provide a mechanism for increased efficacy of conventional antibiotics in these populations.

Bacteria growing as biofilms exhibit increased capacity to ward off antimicrobials. Without wishing to be bound by theory, it is hypothesized that the EPS matrix, which consists of lengthy chains of negatively-charged sugars, acts as a kind of 'surrogate membrane' that electrostatically attracts and binds—or at least physically impedes—incoming antimicrobials before they can reach and damage the bacterial membrane per se. Thus, some conventional antibiotics— notably tobramycin (an aminoglycoside with net charge+5) that is widely employed against *P. aeruginosa* infections— are likely to be bound by the EPS layer. The peptides described herein are unexpectedly and demonstrably highly selective against the negatively-charged bacterial membrane versus the zwitterionic mammalian membranes of a human host.

Additionally, these peptides are similarly attracted to the EPS layer of bacteria. The novel observation has now been made that alginate, the anionic water-soluble exopolysaccharide of *P. aeruginosa*, can bind the peptides described herein and trigger them to undergo 'premature' conformational changes of the type normally associated with CAP insertion into a membrane environment, i.e., induction of α-helical structure. It has further been noted that helical induction in CAP peptides by alginate occurred only for antimicrobially-active peptides, viz., those above the hydrophobicity threshold for membrane insertion. These results are consistent with the notion that alginate and, by extension, biofilms contain not only anionic binding sites, but further resemble membranes via hydrophobic micro-compartments (constituted from the oriented C—H bonds around the sugar rings) that in total offer the same options for CAP interactions as do the structures of the anionic bacterial membranes themselves. It thus appears that alginate 'competes' with the membrane, and 'traps' the peptides by promoting peptide-peptide oligomerization and inactivation before the CAP can ever reach the membrane. As such, the peptides described herein either (i) bypass, at least in part, the EPS while retaining activity at the bacterial membrane; and/or (ii) tightly bind the EPS, causing defects and aggregates in this layer, thereby opening a 'drawbridge' conduit for unbound CAP molecules—along with co-present antibiotics such as tobramycin—to advance readily to the bacterial membrane and exert their effects. These actions are encapsulated by the proposed mechanism shown in FIG. 1 for the designed CAPs when used in combination therapy. Biofilm EPS protects the embedded bacteria from being attacked by antibiotics (top). In combination therapy, the CAPs improve the effectiveness of the small antibiotics against biofilms, by either "weakening" the alginate layer to facilitate membrane access to other conventional antibiotics (lower left); and/or by diffusing themselves through the EPS matrix and binding the membrane of the embedded bacteria, thereby creating a 'dual action' mechanism where both the CAPs and the conventional antibiotics gain access to the bacterial membrane (lower right).

In an aspect, the peptides are stapled into a macrocyle to improve metabolic stability. The peptide may be treated in a reaction, such as a one-step reaction, with a catalyst to convert the peptide into a macrocycle. In an aspect, the peptides are helix-stapled. Examples of peptide stapling methods are found in, for example, U.S. Pat. Nos. 8,586,707, 8,524,669, 8,614,186, 8,685,928, 7,192,713, 7,183,059, and 5,811,515 and U.S. Patent Application Publication Nos. 2013/0281657, 2011/0144306, 2012/0115793, 2012/0141527, 2014/0011746, and 2014/0011747, the disclosures of which are incorporated herein by reference.

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitation.

EXAMPLES

Biofilm Antibacterial Susceptibility Assays
Materials:

| | |
|---|---|
| Bacteria strains | 96-well plates x4 for each test |
| Blood agar plates | Peg lids x1 |
| TSB (Tryptic Soy Broth) | Dilution tubes (comes in a box) |
| MHB | Eppendorf tubes |
| Autoclaved H$_2$O | Multi-channel pipet |

The cationic antimicrobial peptide used in these experiments was the all-D-isomer of KKKKKKAAF-AAWAAFAA-NH$_2$ (SEQ ID NO:3; also referred to in the tables and figures as D-6k-f17), which physically disrupts bacterial membranes. The antibiotics used in these experiments included tobramycin, an aminoglycoside drug that inhibits protein synthesis; ciprofloxacin, a quinolone drug that interferes with DNA replication; and meropenem, a β-lactam drug that inhibits synthesis of the peptidoglycan layer of bacterial cell walls. The clinically isolated *P. aeruginosa* mucoid strains that were used in these experiments are described in Table 1.

TABLE 1

Clinically isolated *P. aeruginosa* mucoid strains

| Sensitive Strains | Resistant Strains |
|---|---|
| SMH 022B5-2 | HSC 003B3-1 |
| SMH 051B3-1 | HSC 020B2-1 |
| SMH 123E1-1 | HSC 027B2-3 |

The planktonic (MICs) and biofilm inhibitory concentrations (BICs) of the designed cationic antimicrobial peptide, KKKKKKAAFAAWAAFAA-NH$_2$ (SEQ ID NO:3; also referred to as D-6k-f17) and the conventional antibiotic tobramycin are shown in Table 2.

TABLE 2

The planktonic (MICs) and biofilm inhibitory concentrations (BICs) of the designed cationic antimicrobial peptide, KKKKKKAAFAAWAAFAA-NH$_2$ (SEQ ID NO: 3; also referred to as D-6k-f17) and tobramycin.

| Clinical P. aeruginosa strains | D-6k-f17 MIC (µg/mL) | D-6k-f17 BIC (µg/mL) | Tobramycin MIC (µg/mL) | Tobramycin BIC (µg/mL) |
|---|---|---|---|---|
| HSC 003B3-1 | 2-4 | 32-64 | 2-8 | 8-64 |
| HSC 020B2-1 | 8-16 | 64 | 32-64 | 128 |
| HSC 027B2-3 | 8-32 | >128 | >128 | >128 |
| SMH 022B5-2 | 2 | 2-4 | ≤0.5 | ≤0.5 |
| SMH 051B3-1 | 2-4 | 2-4 | ≤0.5 | ≤0.5 |
| SMH 123E1-1 | 4 | 4-64 | ≤0.5 | 0.5-1 |

TABLE 3

The planktonic (MICs) and biofilm inhibitory concentrations (BICs) of meropenem and ciprofloxacin.

| | Clinical P. aeruginosa strains | Meropenem MIC (µg/mL) | Meropenem BIC (µg/mL) | Ciprofloxacin MIC (µg/mL) | Ciprofloxacin BIC (µg/mL) |
|---|---|---|---|---|---|
| Resist. | HSC 003B3-1 | ≤0.5 | ≤0.5 | ≤0.5 | ≤0.5 |
| | HSC 020B2-1 | 1-2 | 2 | ≤0.5 | ≤0.5 |
| | HSC 027B2-3 | 2 | 4 | 8-16 | 16-32 |

Methods:

Prep Work—3 Days

Culture the Clinical Mucoid *P. aeruginosa* Strains Isolated from CF Patients

1. Freshly subculture the glycerol stock of the strain (stored at −80° C.) by streaking onto a blood agar (3~4 streaks). Incubate the blood agar plate at 37° C. for 24 hr. The consistency of the mucoid phenotype can be improved by further subculturing (e.g., a total of 3 times, one/day).
2. The following day, pick a few colonies and streak them onto a fresh blood agar.

Note: Every time the cells are cultured using the stock strains (stored at −80° C.), they should be subcultured 3 times in total, and the last blood agar plate is then good for about one week.

In the following week, the strains can be re-subcultured from the last agar plate to grow fresh colonies—this needs only to be done once (no need to do it 3 times). If the mucoid phenotype is lost, the glycerol stocks (−80° C.) should be used, and subcultured 3 times.

Biofilm Assay—Day 1

Grow Overnight Cell Culture

1. Inoculate freshly cultured cells (see prep work) in 10 mL TSB, and grow overnight at 37° C. on a shaker.

Antibiotic Plate Set-up (a) If only one antibiotic is being testing against, then serial dilutions of test peptides or antibiotics are made at desired concentrations in 150 µL MHB.

(b) If a combination of antibiotics is being tested against, then:

Prepare the first antibiotic in an Eppendorf tube (8 different concentrations)

First tube >8 (columns)×15 (each well)×2 (first tube needs 2× volume) µL of peptide at 10× highest concentration (i.e. 1280 µg/mL), say 260 µL.

Add half of the volume from above (i.e., 130 µL) of autoclaved H$_2$O in the next 7 tubes.

Serial dilution from the second to the last tube.

Add 15 µL of peptide solution to each well of a 96-well antibiotic plate, from left to right (same concentration for each column, i.e., 15 µL of 1280 µg/mL to each of the first column).

Prepare the second antibiotic in Eppendorf tube (8 different concentrations)

First tube needs also >8×15×2 µL of peptide at 10× highest concentration (i.e., 1280 ug/mL), say 260 µL.

Add half of the volume from above (i.e., 130 µL) of autoclaved H$_2$O in the next 7 tubes.

Serial dilution from the second to the last tube.

Add 15 µL of peptide solution to each well of the same antibiotic plate containing the first antibiotic, from top to bottom (same concentration for each row, i.e., 15 µL of 1280 µg/mL to each of the first row).

The highest concentration combo is at the top left corner, and the lowest concentration combo is at the bottom right corner on the plate.

Use a multi-channel pipet, add 120 µL MHB to each well, total volume=150 µL

Controls=150 µL MHB only; no peptides/antibiotics.

(c) If the same combination of antibiotics is being tested in more than one plate, then:

Prepare the first antibiotic in dilution BOX 1 (dilution tubes):

First column (i.e., A2→H2)=n×30 µL of peptide at 10× highest concentration (i.e., 1280 µg/mL), where n=number of plates.

Place n×15 µL autoclaved H$_2$O in other tubes.

Serial dilution from the second to the last column using a multi-channel pipet.

Remove half of the solution in the last column.

Prepare the second antibiotic in dilution BOX 2 (dilution tubes):

First row (i.e., A2→A9)=n×40 µL (need more than 2×15 µL, so we will have enough when we transfer) of second peptide at 10× highest concentration (i.e., 1280 µg/mL), where n=number of plates.

Place n×20 µL autoclaved H$_2$O in other tubes.

Serial dilution from the second to the last row using a multi-channel pipet.

Remove half of the solution in last column.

Using a multi-channel pipet, add n×15 µL of BOX2 to the corresponding tubes in BOX1 (now BOX 1 contains both antibiotics at 10× concentration each).

Add n×120 µL MHB to each tube in BOX 1, total volume in each tube=n×150 µL.

Transfer 150 µL of mixture to each 96-well antibiotic plate.

Controls=150 µL MHB in the well of each plate; no peptides/antibiotics.

Biofilm Assay—Day 2

Biofilm Set-up
1. Make 0.5 McFarland for each strain/organism (add ~100 µL O/N culture to 2 mL 50% TSB): 0.5 McFarland=$10^8$ CFU/mL.

To calibrate a colourimeter/turbidity meter:

Positive blank: place a solid marker in the holder; turn the left knob to adjust to zero.

Negative blank: use a glass tube containing 50% TSB (1:1 TSB/$H_2O$); adjust the right knob to 100% T.

Non-mucoid strains should be read in the lower 'red zone' on a colorimeter/turbidity meter.

Mucoid strains should be a bit heavier, and read in the mid 'red zone'.

2. Make bacterial inoculums: to a 50 mL falcon tube, add 300 µL of 0.5 McFarland to 19.7 mL of TSB.
3. Mix the tube gently by inverting.
4. In the biosafety fume hood or beside the flame:

Label a 96-well plate: strain and time.

Pour inoculum into a reservoir.

Using the multi-channel pipet, add 150 µL of inoculum into each well, leave the last column empty (last column=negative control, no cells).

Carefully place a peg lid onto the plate, match the cut corners.

5. Place the plate on a shaker in 37° C. incubator (requires ≥3 h).

Checking Biofilm Plate Growth
1. Check plates periodically using a plate-reader to determine OD readings:

At $OD_{650}$, aim for ~0.045-0.050.

Depending on the strain, require 3-28 h to grow. The HSC 003, HSC 020, and HSC 027 strains require 3~4 h.

Figure 2:
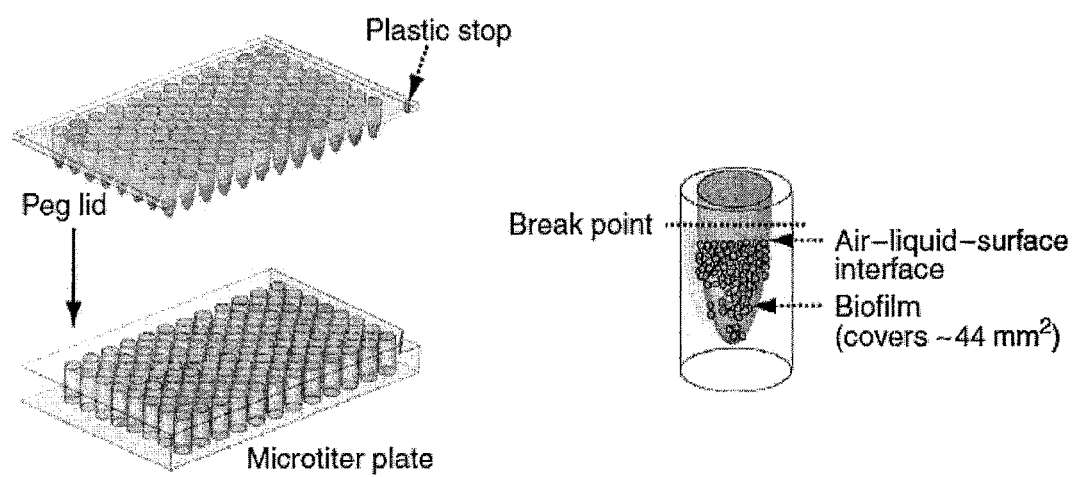
FIG. 2 is a schematic drawing of the method used in Example 1.
Figure 3:
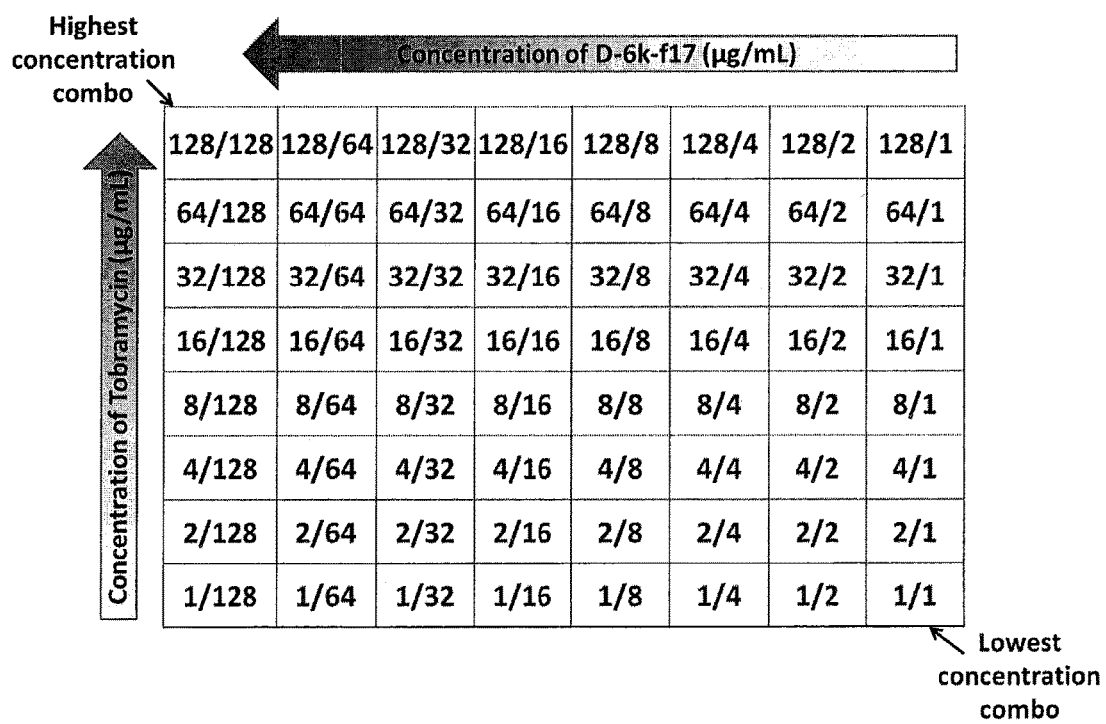
FIG. 3 shows a template of how the experiments described herein were set up.

Loading Antibiotic Plates
1. Place the peg lid (containing biofilm growth) of the susceptibility plate into a pre-made 96-well antibiotic plate (see protocol from Day 1; see FIG. 1). The combination therapies were tested according to the template shown in FIG. 2. Incubate at 37° C. for 24 h.

* This will be referred to the planktonic growth plate, which measures the planktonic susceptibility in the biofilm assay, or MICs. *

2. Place the lid of 96-well antibiotic plate onto the previous susceptibility plate, and keep in the fridge for reference until the experiment is completed.
3. Proceed to perform inoculum check (see below)

Inoculum Check
1. Purity check:

Take a loopful of bacteria culture from any well of the susceptibility plate.

Spread onto half of a blood agar plate.

Place in the incubator at 37° C. for 24 h.

2. Inoculum check:

In sterile Eppendorf tubes or liver vials (need 4 per strain), prepare the following dilutions:

a. $10^2$: 200 µL of $H_2O$ and 50 µL of inoculum from any well of the susceptibility plate.

b. $10^3$: 900 µL of $H_2O$ and 100 µL of mixture from Step (a).

c. $10^4$: 900 µL of $H_2O$ and 100 µL of mixture from Step (b).

d. $10^5$: 900 µL of $H_2O$ and 100 µL of mixture from Step (c).

Split blood agar plates into quadrants: two for $10^4$ and two for $10^5$.

Take 50 µL from Step (c) or Step (d) and place onto blood agar plates.

Let dry for about 30 min in the hood with the lid closed, and then incubate upside-down at 37° C. for 18~24 h.

Biofilm Assay—Day 3

Recovery Plate
1. Prepare wash plates (multi-channel pipet 200 µL autoclaved $H_2O$ to each well).
2. Prepare recovery plates (multi-channel pipet 150 µL MHB to each well).
3. Take biofilm pegs and place into wash plate, let sit for one min. Save the incubated planktonic growth plate for later use.
4. Take the biofilm peg lids and place into recovery plate. Incubate at 37° C. for 24 h.

* This will be referred to the biofilm recovery plate, which measures the biofilm inhibitory concentrations or BICs.*

5. Read biofilm planktonic growth plate using a mirror under light (the rest of the room needs to be dark):

Cloudy wells=growth.

Clear wells=no growth.

If the growth is hard to see, allow to incubate for longer:

If the positive control has visible growth, but not the antibiotic treated wells, then incubate at room temperature overnight to confirm.

If the positive control also has no visible growth yet, then incubate at 37° C. overnight, and check again.

6. Check inoculum plates:

Purity plate: check to see if the phenotypes in the colonies are consistent.

Inoculum plate: count the number of colonies in $10^4$ and/or $10^3$ quadrants; aim for ~5×$10^5$ CFU/mL (~5 colonies in $10^5$).

Biofilm Assay—Day 4

Read biofilm recovery plate.

Results:

Example 1

Figure 4:
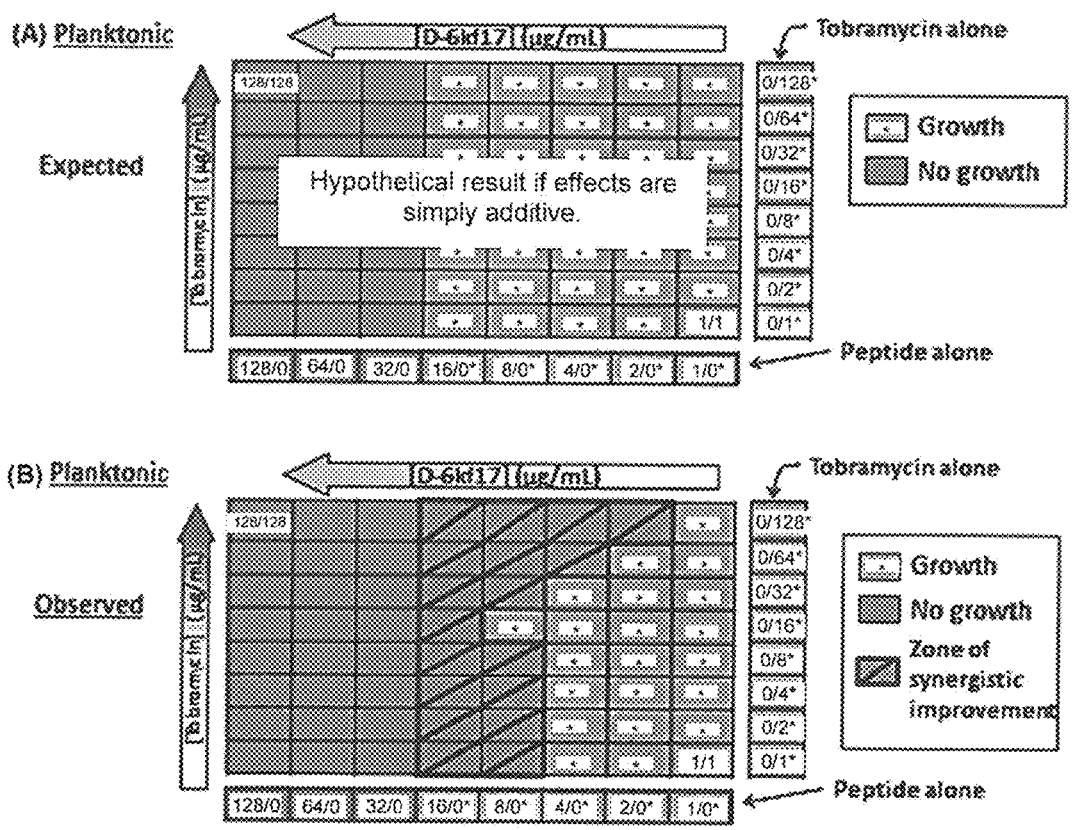
FIG. 4 shows (A) the predicted and (B) the observed results for CAP D-6k-f17 and the antibiotic tobramycin used in a combination therapy experiment against a resistant P. aeruginosa strain HSC027 isolated from CF patients in planktonic form.
Figure 5:
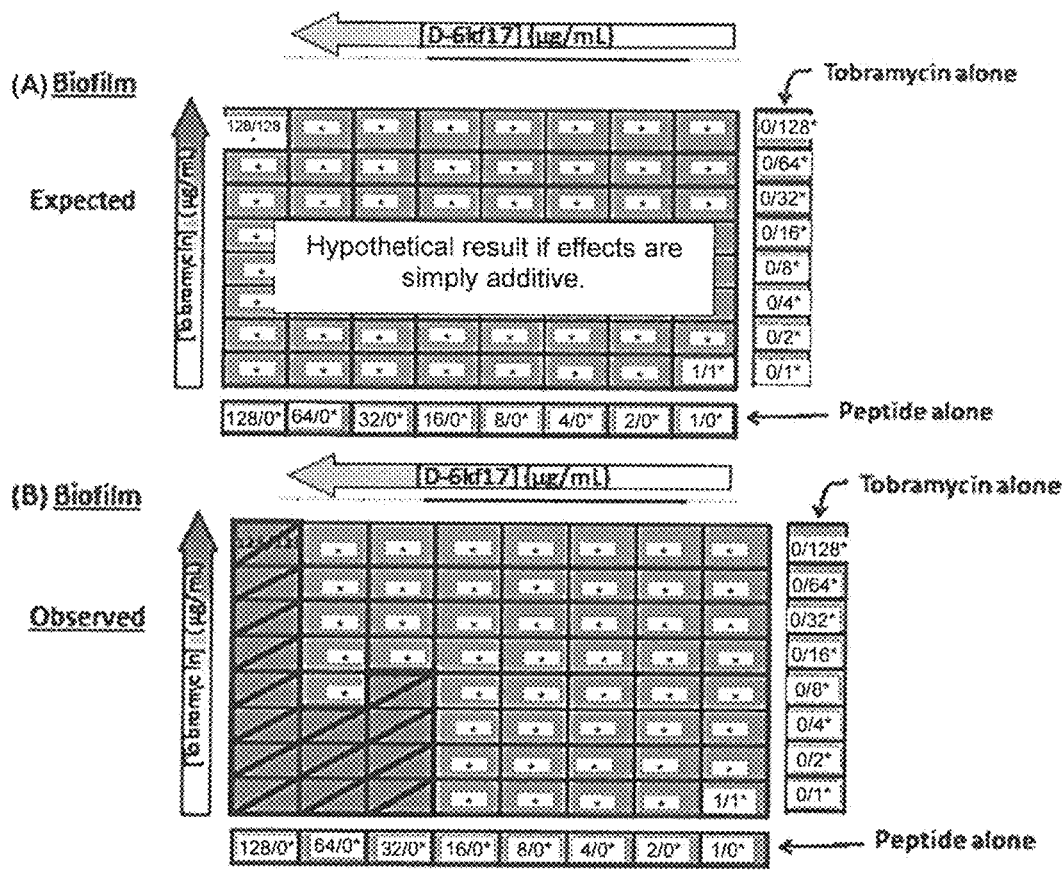
FIG. 5 shows (A) the predicted and (B) the observed results for CAP D-6k-f17 and the antibiotic tobramycin used in a combination therapy experiment against a resistant P. aeruginosa strain HSC027 isolated from CF patients in biofilm form.

FIGS. 4 and 5 show the results of a combination therapy experiment in which CAP D-6k-f17 and the conventional antibiotic tobramycin were used against a resistant *P. aeruginosa* strain (HSC027) isolated from CF patients in both planktonic (FIG. 4) and biofilm forms (FIG. 5). The concentration of CAP increases from right-to-left along the grid (1 to 128 µg/mL), whereas the concentration of tobramycin increases from bottom-to-top (1 to 128 µg/mL). Thus, the 'concentration combination' is lowest at the bottom right well (1 µg/mL CAP+1 µg/mL tobramycin), and highest at the top left well (128 µg/mL CAP+128 µg/mL tobramycin). If there were only an additive effect, as shown hypothetically in FIG. 4A and FIG. 5A, the growth on the plate would match the simple sum of the killing efficacy of each drug alone. However, the observed results, given in FIG. 4B and FIG. 5B, show an added (cross-hatched) zone of inhibited growth, representing a zone of synergistic improvement when the two drugs were combined together in the treatment. The 'zone of synergy' is defined as the wells that initially show growth (green wells) when treated with either antibiotic alone, but now display no growth (red wells).

Example 2

Figure 6:
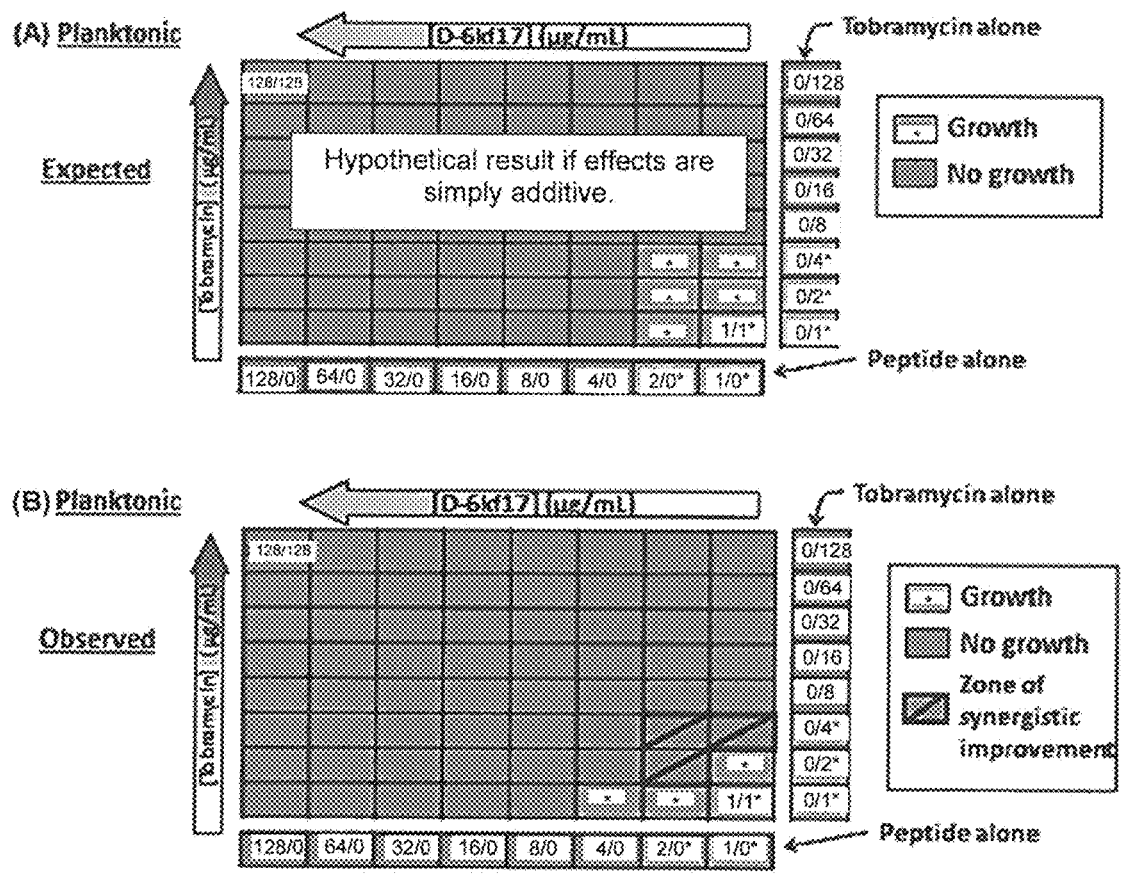
FIG. 6 shows (A) the predicted and (B) the observed results for CAP D-6k-f17 and the antibiotic tobramycin used in a combination therapy experiment against a resistant P. aeruginosa strain HSC003 isolated from CF patients in planktonic form.
Figure 7:
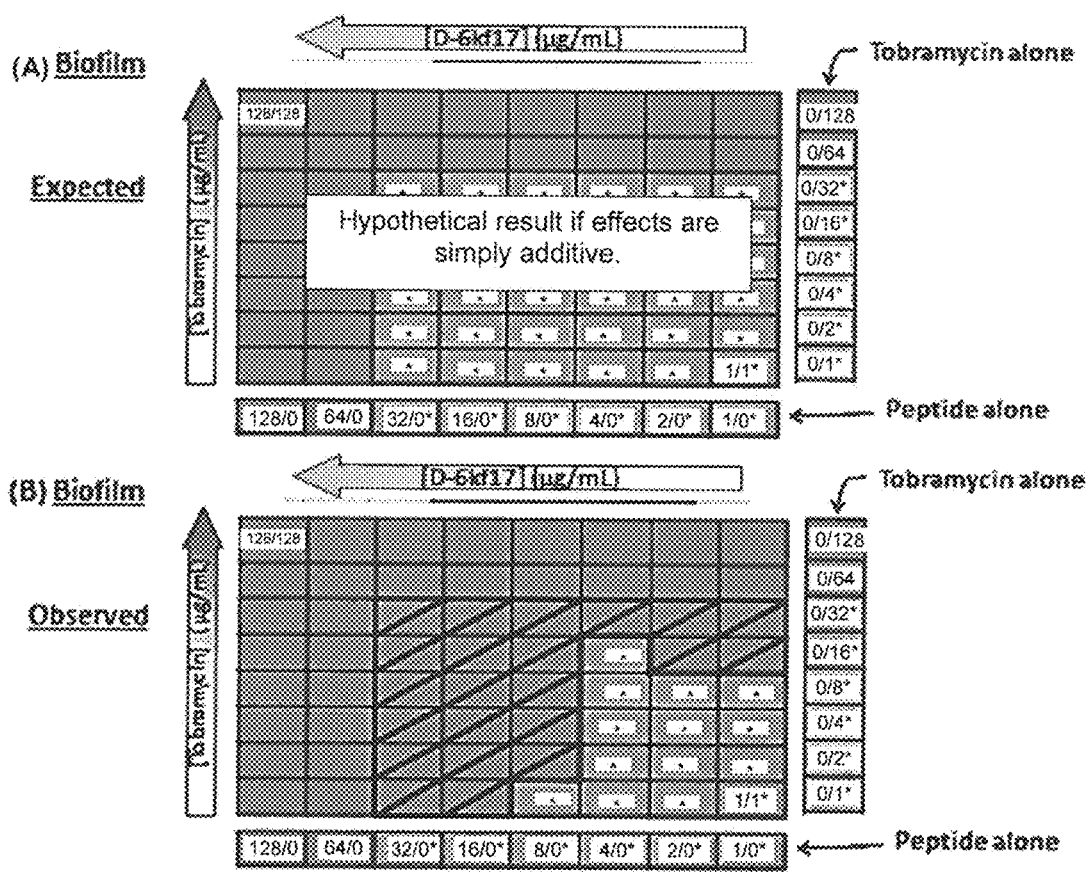
FIG. 7 shows (A) the predicted and (B) the observed results for CAP D-6k-f17 and the antibiotic tobramycin used in a combination therapy experiment against a resistant P. aeruginosa strain HSC003 isolated from CF patients in biofilm form.

FIGS. 6 and 7 show the results of combination therapy experiments with D-6kf17 and the conventional antibiotic tobramycin as described above in Example 1, except that the resistant *P. aeruginosa* strain isolated from CF patients is the planktonic and biofilm forms of the HSC003 strain. As above, if there were only an additive effect, as shown hypothetically in 6A (planktonic form) and FIG. 7A (biofilm form), the growth on the plate would match the simple sum of the killing efficacy of each drug alone. However, the observed results, given in the graphs of FIG. 6B and FIG. 7B, show an added (cross-hatched) zone of inhibited growth, representing a zone of synergistic improvement when the two drugs were combined together in the treatment.

Example 3

Figure 8:
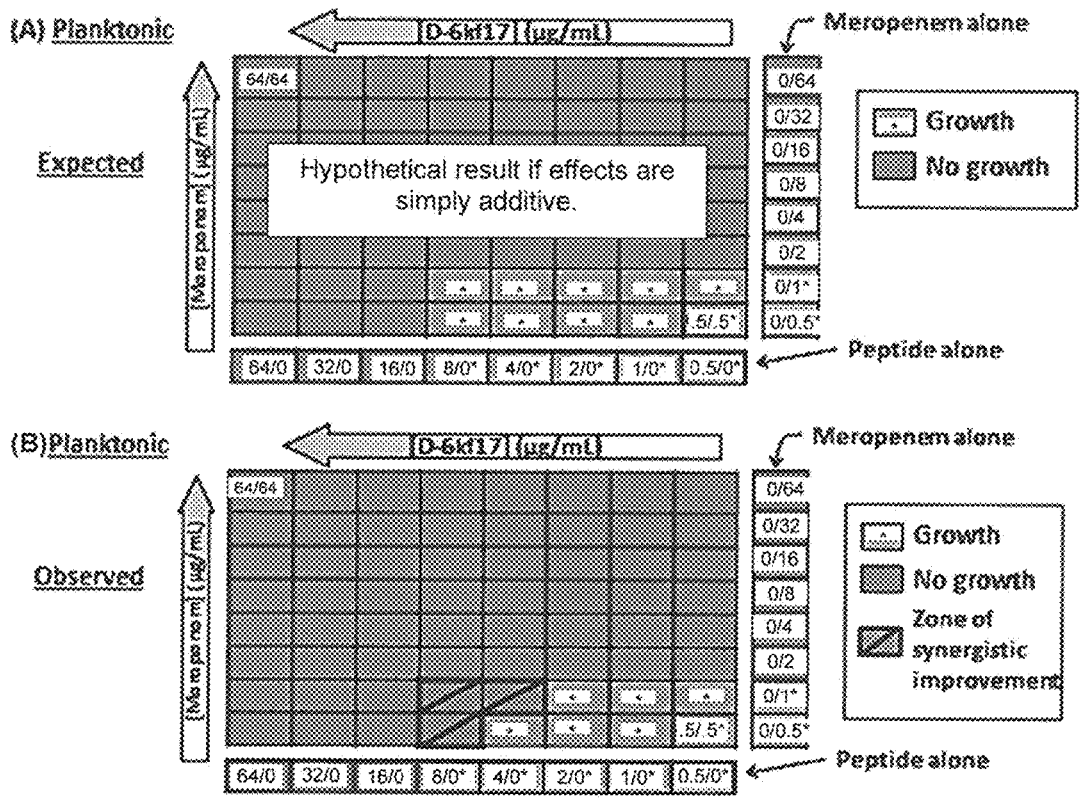
FIG. 8 shows (A) the predicted and (B) the observed results for CAP D-6k-f17 and the antibiotic meropenem used in a combination therapy experiment against a resistant P. aeruginosa strain HSC020 isolated from CF patients in planktonic form.
Figure 9:
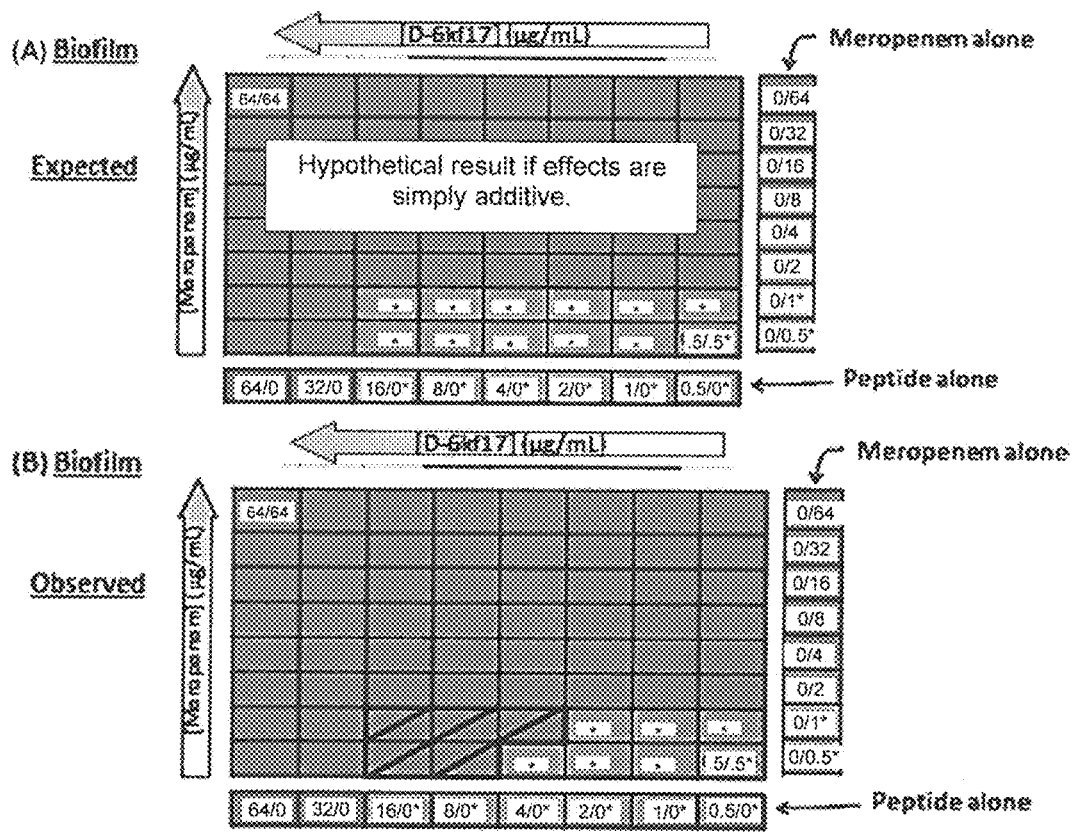
FIG. 9 shows (A) the predicted and (B) the observed results for CAP D-6k-f17 and the antibiotic meropenem used in a combination therapy experiment against a resistant P. aeruginosa strain HSC020 isolated from CF patients in biofilm form.

FIGS. 8 and 9 show the results of combination therapy experiments as described above in Example 1, except that the resistant *P. aeruginosa* strain isolated from CF patients is the HSC020 strain and the antibiotic is merepenem. As above, if there were only an additive effect, as shown hypothetically in the graphs of FIG. 8A (planktonic form) and FIG. 9A (biofilm form), the growth on the plate would match the simple sum of the killing efficacy of each drug alone. However, the observed results, given in FIG. 8B and FIG. 9B, show an added (cross-hatched) zone of inhibited growth, representing a zone of synergistic improvement when the two drugs were combined together in the treatment.

Example 4

Figure 10:
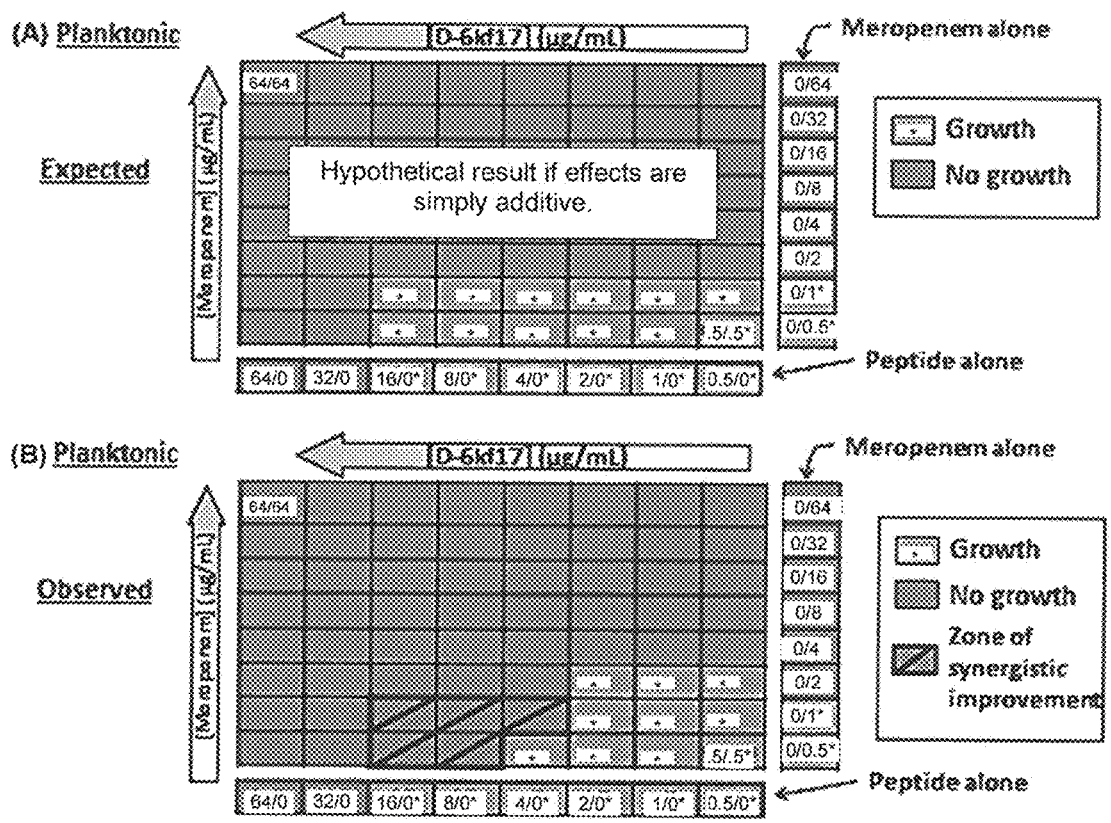
FIG. 10 shows (A) the predicted and (B) the observed results for CAP D-6k-f17 and the antibiotic meropenem used in a combination therapy experiment against a resistant P. aeruginosa strain HSC027 isolated from CF patients in planktonic form.
Figure 11:
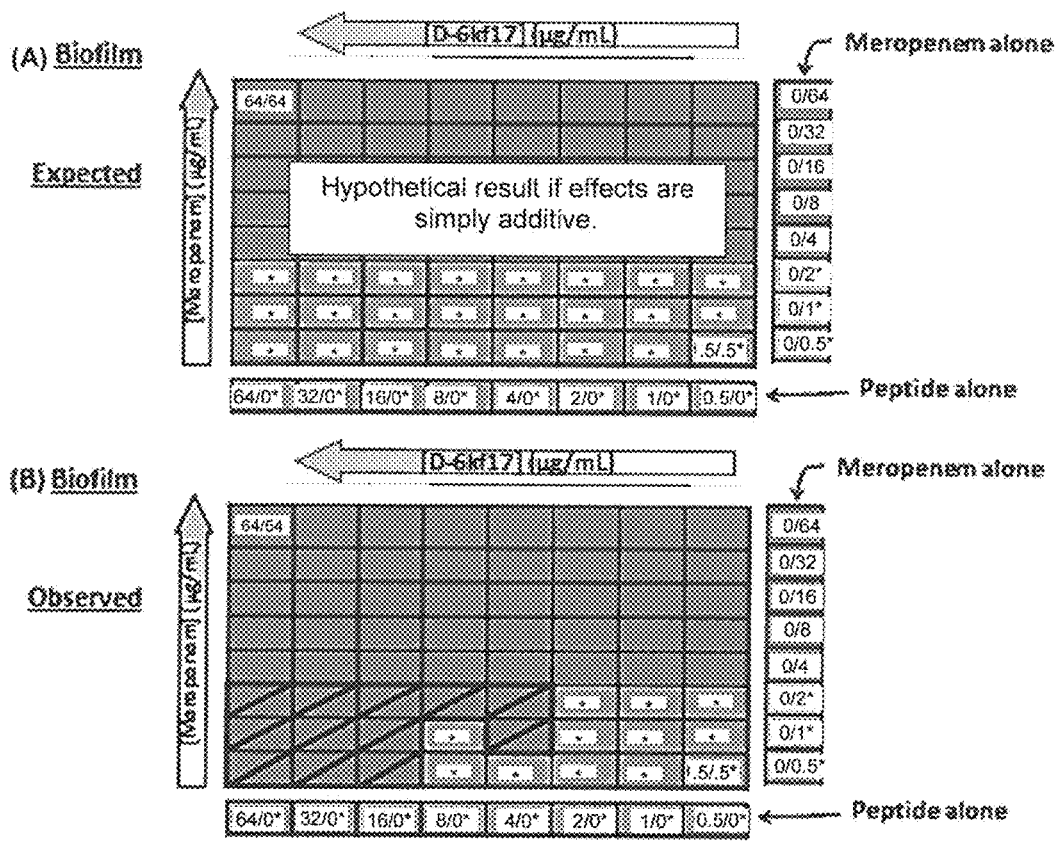
FIG. 11 shows (A) the predicted and (B) the observed results for CAP D-6k-f17 and the antibiotic meropenem used in a combination therapy experiment against a resistant P. aeruginosa strain HSC027 isolated from CF patients in biofilm form.

FIGS. 10 and 11 show the results of combination therapy experiments as described above in Example 1 with resistant strain HSC027, except that the conventional antibiotic is merepenem. As above, if there were only an additive effect, as shown hypothetically in FIG. 10A (planktonic form) and FIG. 11A (biofilm form), the growth on the plate would match the simple sum of the killing efficacy of each drug alone. However, the observed results, given in the graphs of FIG. 10B and FIG. 11B, show an added (cross-hatched) zone of inhibited growth, representing a zone of synergistic improvement when the two drugs were combined together in the treatment.

Example 5

Figure 12:
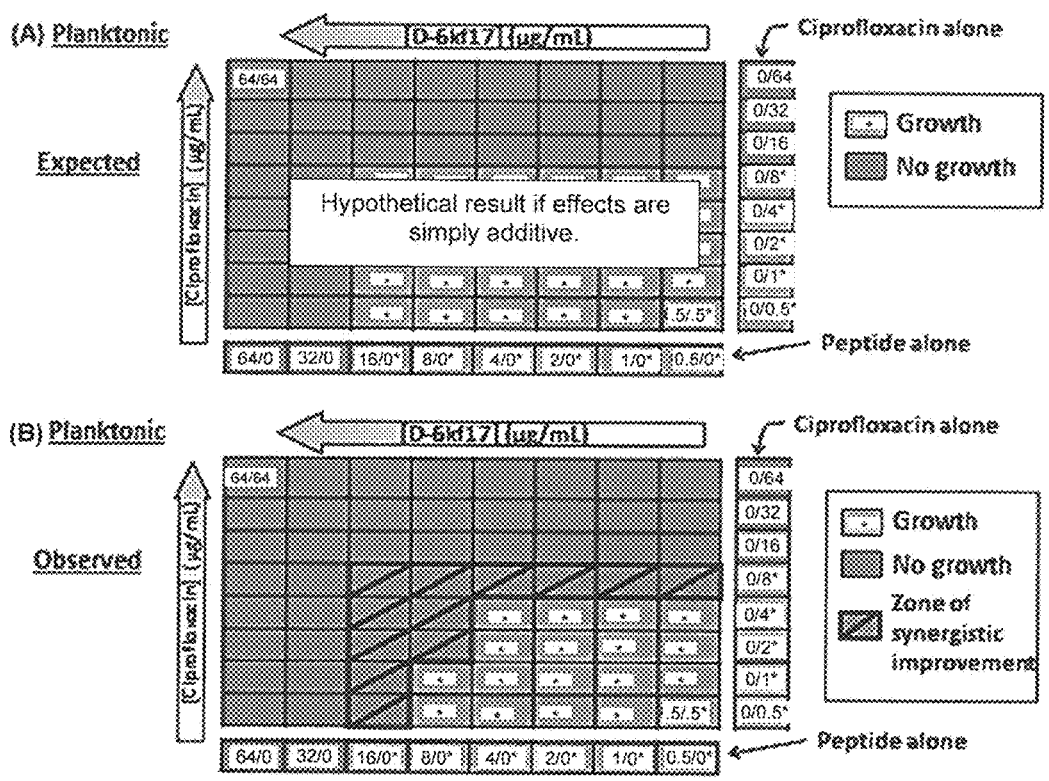
FIG. 12 shows (A) the predicted and (B) the observed results for CAP D-6k-f17 and the antibiotic ciprofloxacin used in a combination therapy experiment against a resistant P. aeruginosa strain HSC027 isolated from CF patients in planktonic form.
Figure 13:
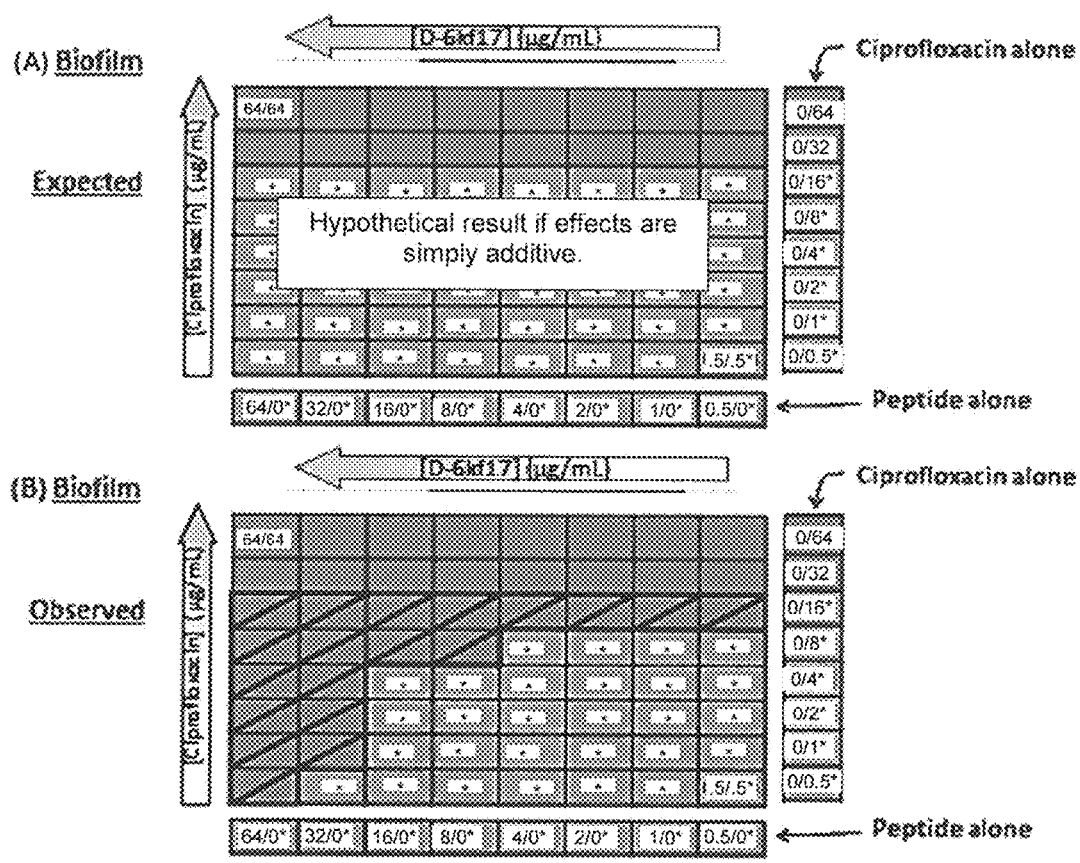
FIG. 13 shows (A) the predicted and (B) the observed results for CAP D-6k-f17 and the antibiotic ciprofloxacin used in a combination therapy experiment against a resistant P. aeruginosa strain HSC027 isolated from CF patients in biofilm form.

FIGS. 12 and 13 show the results of a combination therapy experiment as described above in Example 1 with resistant strain HSC027, except that the conventional antibiotic is ciprofloxacin. As above, if there were only an additive effect, as shown hypothetically in FIG. 12A (planktonic form) and FIG. 13A (biofilm form), the growth on the plate would match the simple sum of the killing efficacy of each drug alone. However, the observed results, given in FIG. 12B and FIG. 13B, show an added (cross-hatched) zone of inhibited growth, representing a zone of synergistic improvement when the two drugs were combined together in the treatment.

Example 6

Figure 14:
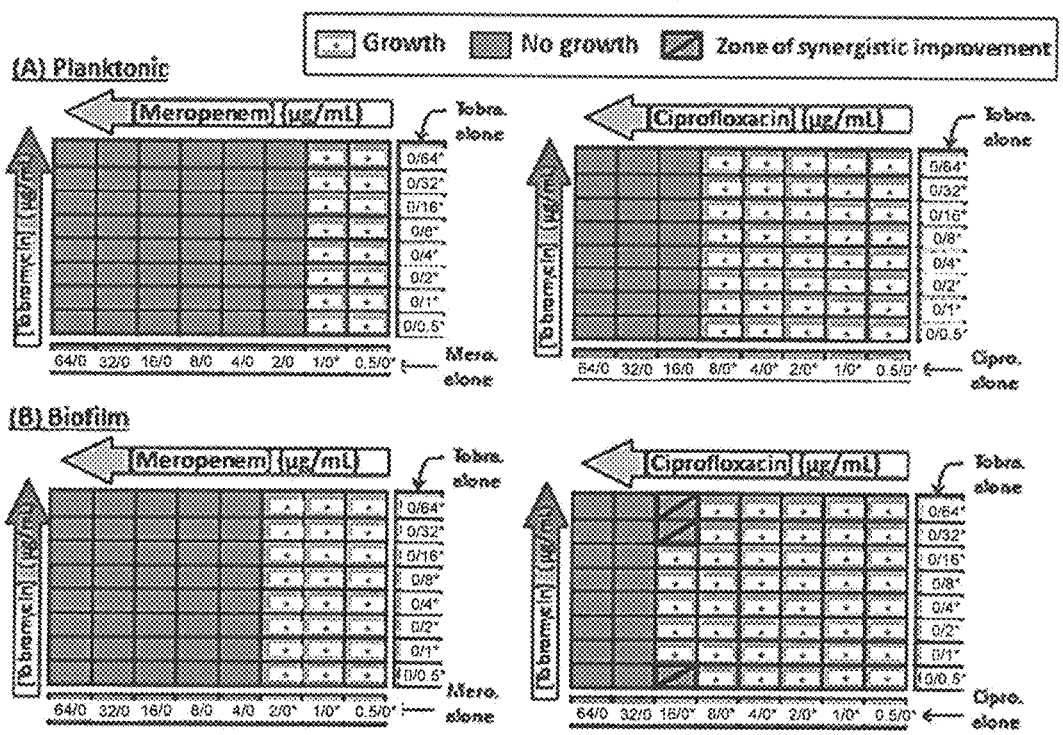
FIG. 14 shows the observed results for tobramycin and meropenem or ciprofloxacin used in a combination therapy experiment against a resistant P. aeruginosa strain HSC027 isolated from CF patients in both (A) planktonic and (B) biofilm forms.
Figure 15:
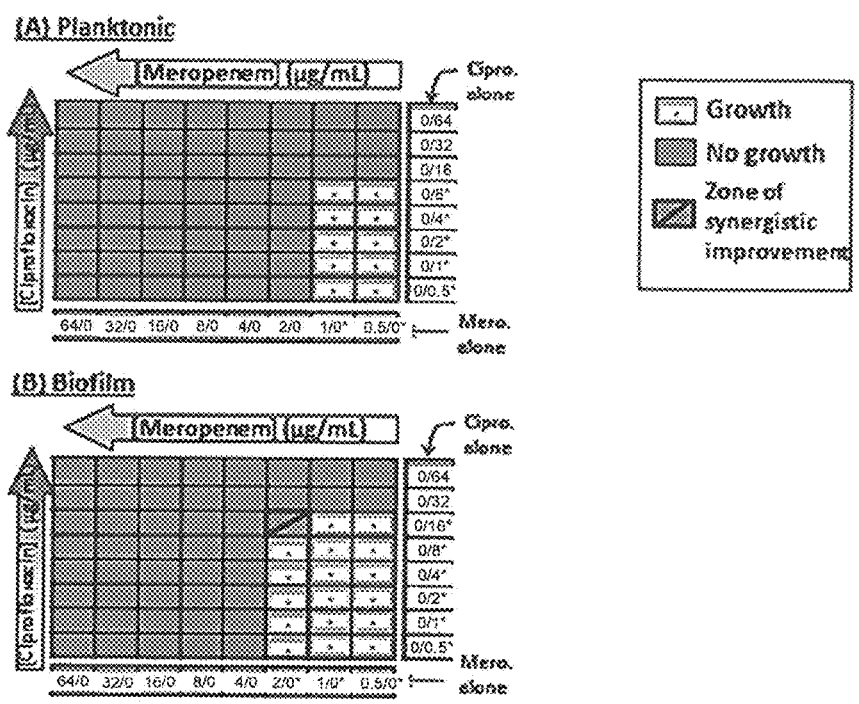
FIG. 15 shows the observed results for meropenem and ciprofloxacin used in a combination therapy experiment against a resistant P. aeruginosa strain HSC027 isolated from CF patients in both (A) planktonic and (B) biofilm forms.
Figure 16:
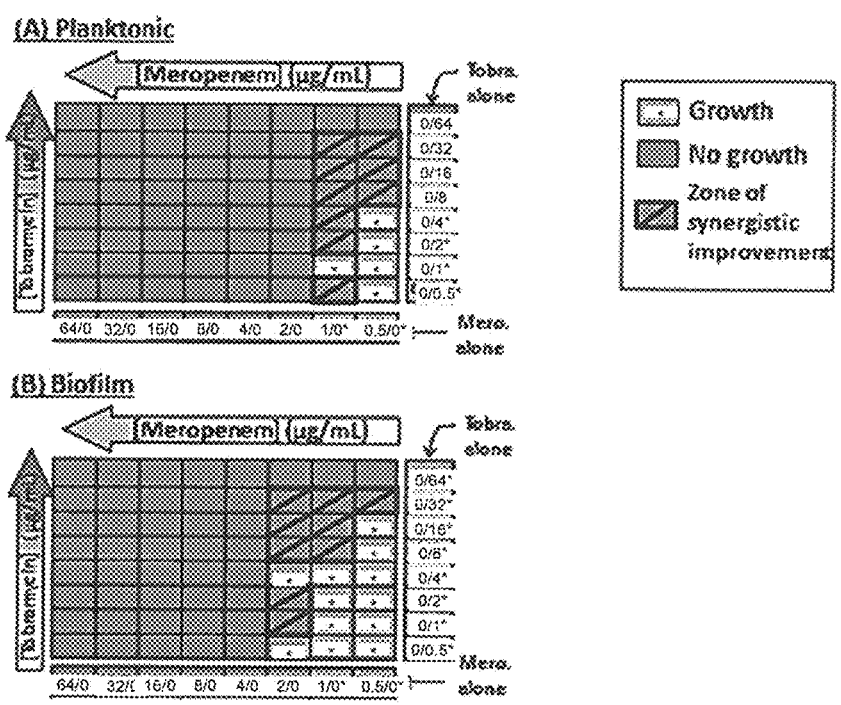
FIG. 16 shows the observed results for meropenem and tobramycin used in a combination therapy experiment against a resistant P. aeruginosa strain HSC020 isolated from CF patients in both (A) planktonic and (B) biofilm forms.

FIGS. 14, 15, and 16 show the results of combination therapy experiments where different conventional antibiotics were used together. It can be seen that the combined effects of these antibiotics were generally simply additive in nature.

Hemolysis Assays
Materials/Methods:

Freshly collected human blood with heparin was centrifuged to remove the buffy coat, and the erythrocytes obtained were washed three times with phosphate-buffered saline (PBS), centrifuged for 10 min at 1,000×g, and resuspended in PBS to 4% (vol/vol). Peptides were diluted in PBS to 400 and 100 mM, and 100 ml of the erythrocyte suspension and 100 ml of the peptide/antibiotic solution were added to the wells of a 96-well round-bottomed polypropylene microtiter plate. Peptide or antibiotic concentrations were tested up to 128 μg/mL. PBS and 0.1% Triton X-100 were used as control agents for 0 and 100% hemolysis, respectively. Plates were incubated for 1 h at 37° C. and centrifuged at 1,000×g for 5 min. Supernatant (100 ml) was transferred to a 96-well flat-bottomed polystyrene plate, and the release of hemoglobin was monitored by measuring the absorbance at 540 nm in a microplate reader.

Results:

Table 4 shows the results of these experiments. It can be seen that each of the agents alone could be administered at a concentration of up to 128 μg/mL without causing hemolysis, either individually or in various combinations as shown in Table 4.

TABLE 4

Hemolysis results of antibiotics alone and in combination.

| Antibiotics | Maximum Hemolytic Concentration (MHC) * |
| --- | --- |
| D-6kf17 | >128 μg/mL |
| Tobramycin | >128 μg/mL |
| Meropenem | >128 μg/mL |
| Ciprofloxacin | >128 μg/mL |
| D-6kf17 + Tobramycin | >128/128 μg/mL |
| D-6kf17 + Meropenem | >128/128 μg/mL |
| D-6kf17 + Ciprofloxacin | >128/128 μg/mL |
| Tobramycin + Meropenem | >128/128 μg/mL |
| Tobramycin + Ciprofloxacin | >128/128 μg/mL |
| Meropenem + Ciprofloxacin | >128/128 μg/mL |

* MHC is the highest nonhemolytic concentration.

Time Course Assays
Materials/Methods:

*P. aeruginosa* cells are treated with the peptides described herein at 4× MICs; aliquots are removed at 10 min intervals, diluted, and plated for the determination of viable counts. Conventional antibiotics, such as tobramycin, meropenem, and ciprofloxacin, are tested for comparison.

Results:

Preliminary results show that D-6kf17 is able to completely kill the planktonic bacteria in 40 min., while other conventional antibiotics need much longer times.

Example 7

Figure 17:
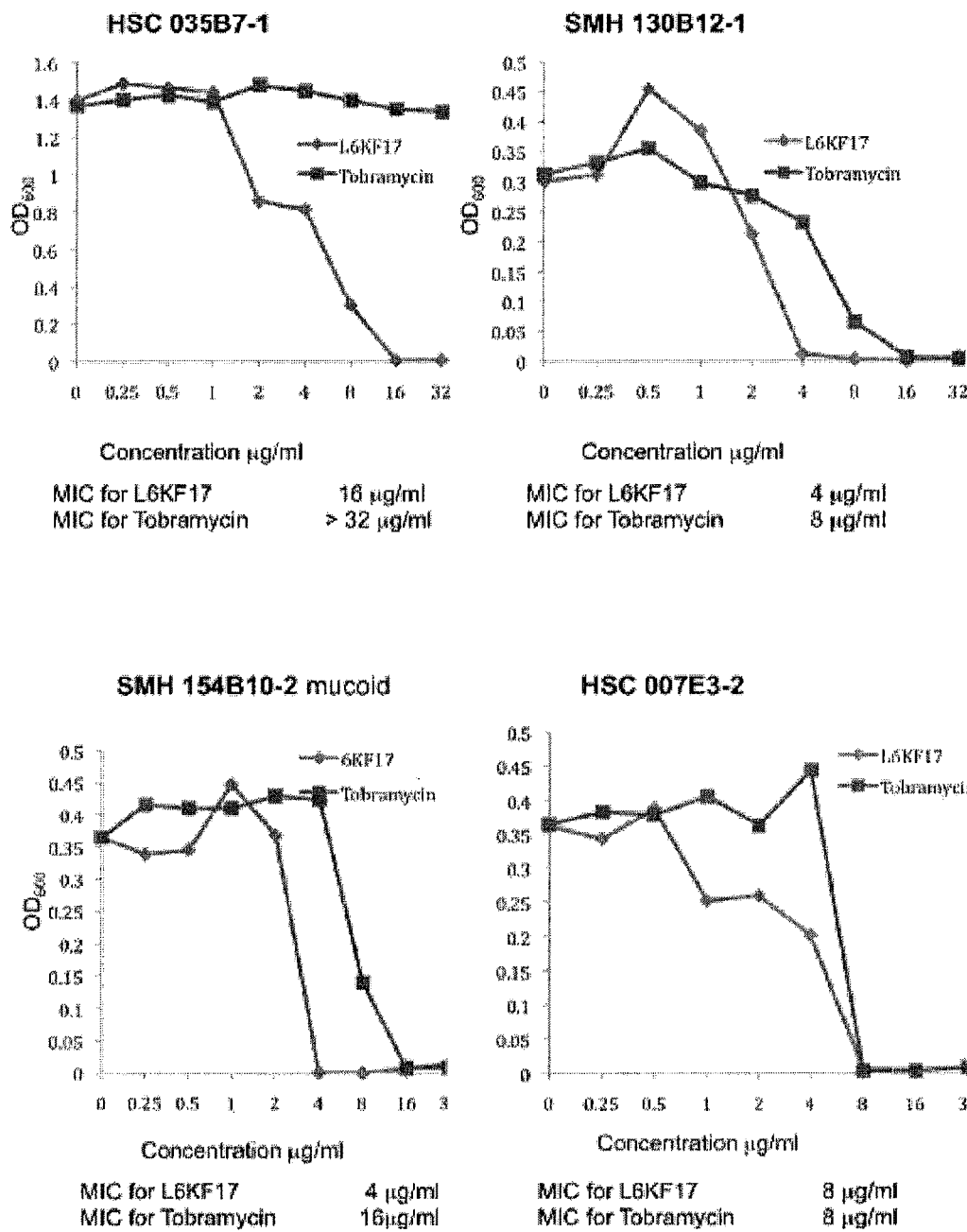
FIG. 17 shows graphs of the MIC values obtained when L6K-F17 and tobramycin were tested for their respective abilities to inhibit growth of selected P. aeruginosa sensitive and mucoid strains. MICs (μg/ml, x-axis) for each compound are shown below each graph. Lower MICs indicate superior growth inhibition. The OD at 600 nm quantitates the extent of bacterial growth. Diamonds=L6K-F17; squares=tobramycin. Incubation: 37° C. for 19-24 hours.

Nine different clinical *P. aeruginosa* isolates were tested with a representative CAP, L-6KF17. It was found that some strains were more sensitive to L-6KF17 ("SMH") than others ("HSC"), as shown in Table 5. Furthermore, L-6KF17 was found to be equal to or superior to tobramycin in most cases, and was particularly useful in two separate strains that were resistant to tobramycin. Representative graphs of these MIC results are shown in FIG. 17.

TABLE 5

Antimicrobial activities of L-6KF17 and tobramycin against clinical strains of *P. aeruginosa*.

| No. | *P. aeruginosa* | MIC (µg/ml)* | |
|---|---|---|---|
| | | L-6KF17 | Tobramycin |
| 1 | SMH 130B12-1 | 4 | 8 |
| 2 | SMH 064B15-2 | 2 | 2 |
| 3 | SMH 072B5-2 | 4 | >32 |
| 4 | HSC 002B10-2 | 8 | 1 |
| 5 | HSC 004B1-3 | 16 | 8 |
| 6 | HSC 007E3-2 | 8 | 8 |
| 7 | HSC 035B7-1 | 16 | >32 |
| 8 | SMH 154B10-2 | 4 | 16 |
| 9 | SMH 112B41 | 8 | 2 |

*MIC is the minimum inhibitory concentration, defined as the lowest antimicrobial agent concentration required to fully inhibit bacterial growth, as tested against *P. aeruginosa*

The above disclosure generally describes the present invention. Although specific terms have been employed herein, such terms are intended in a descriptive sense and not for purposes of limitation.

All publications, patents and patent applications are herein incorporated by reference in their entirety to the same extent as if each individual publication, patent or patent application was specifically and individually indicated to be incorporated by reference in its entirety.

Although exemplary aspects of the invention have been described herein in detail, it will be understood by those skilled in the art that variations may be made thereto without departing from the spirit of the invention or the scope of the appended claims.

The invention claimed is:

1. A method for penetrating a bacterial biofilm, the method comprising administering a peptide to a biofilm, the peptide consisting of the amino acid sequence KKKKKKAAFAAWAAFAA-NH$_2$ (SEQ ID NO:3), wherein penetrating comprises binding to and passing through the bacterial biofilm.

2. The method of claim 1, wherein the amino acids in the peptide are D-amino acids, L-amino acids, or a combination thereof.

3. The method of claim 1, wherein the peptide is a stapled peptide.

4. The method of claim 3, wherein the stapled peptide is a helix stapled peptide.

5. The method of claim 1 wherein the peptide is administered in synergistic combination with an antibiotic.

6. The method of claim 5, wherein the antibiotic is selected from the group consisting of aminoglycosides, fluoroquinolones, carbapenem beta-lactam antibiotics, and combinations thereof.

7. The method of claim 6, wherein the antibiotic is selected from tobramycin, ciprofloxacin, meropenem, and combinations thereof.

8. The method of claim 1, wherein the bacterial biofilm is associated with sinusitis, a urinary tract infection, a middle-ear infection, dental plaque, gingivitis, contact lenses, endocarditis, cystic fibrosis, permanent indwelling devices such as joint prostheses, heart valves, catheters, and intrauterine devices, cutaneous wounds, or a surface that requires cleaning.

9. A method of decreasing the pathology of a *P. aeruginosa* infection associated with a bacterial biofilm in a subject, the method comprising administering a composition comprising a peptide consisting of the amino acid sequence KKKKKKAAFAAWAAFAA-NH$_2$ (SEQ ID NO:3) and an antibiotic selected from the group consisting of tobramycin, ciprofloxacin, and meropenem to the subject, wherein the peptide binds to and passes through the bacterial biofilm.

* * * * *

SEQUENCE LISTING

```
<160> NUMBER OF SEQ ID NOS: 21

<210> SEQ ID NO 1
<211> LENGTH: 17
<212> TYPE: PRT
<213> ORGANISM: Artificial
<220> FEATURE:
<223> OTHER INFORMATION: Cationic antimicrobial peptide
<220> FEATURE:
<221> NAME/KEY: MISC_FEATURE
<222> LOCATION: (7)..(8)
<223> OTHER INFORMATION: Xaa can be A, L, G, or S
<220> FEATURE:
<221> NAME/KEY: MISC_FEATURE
<222> LOCATION: (10)..(11)
<223> OTHER INFORMATION: Xaa can be A, L, G, or S
<220> FEATURE:
<221> NAME/KEY: MISC_FEATURE
<222> LOCATION: (13)..(14)
<223> OTHER INFORMATION: Xaa can be A, L, G, or S
<220> FEATURE:
<221> NAME/KEY: MISC_FEATURE
<222> LOCATION: (16)..(17)
<223> OTHER INFORMATION: Xaa can be A, L, G, or S
<220> FEATURE:
<221> NAME/KEY: MOD_RES
<222> LOCATION: (17)..(17)
<223> OTHER INFORMATION: AMIDATION

<400> SEQUENCE: 1

Lys Lys Lys Lys Lys Lys Xaa Xaa Phe Xaa Xaa Trp Xaa Xaa Phe Xaa
1               5                   10                  15

Xaa

<210> SEQ ID NO 2
<211> LENGTH: 17
<212> TYPE: PRT
<213> ORGANISM: Artificial
<220> FEATURE:
<223> OTHER INFORMATION: Cationic antimicrobial peptide
<220> FEATURE:
<221> NAME/KEY: MISC_FEATURE
<222> LOCATION: (8)..(8)
<223> OTHER INFORMATION: Xaa can be A or L
<220> FEATURE:
<221> NAME/KEY: MISC_FEATURE
<222> LOCATION: (11)..(11)
<223> OTHER INFORMATION: Xaa can be A or L
<220> FEATURE:
<221> NAME/KEY: MISC_FEATURE
<222> LOCATION: (13)..(13)
<223> OTHER INFORMATION: Xaa can be A or L
```

```
<220> FEATURE:
<221> NAME/KEY: MISC_FEATURE
<222> LOCATION: (16)..(16)
<223> OTHER INFORMATION: Xaa can be A or L
<220> FEATURE:
<221> NAME/KEY: MOD_RES
<222> LOCATION: (17)..(17)
<223> OTHER INFORMATION: AMIDATION

<400> SEQUENCE: 2

Lys Lys Lys Lys Lys Lys Ala Xaa Phe Ala Xaa Trp Xaa Ala Phe Xaa
1               5                   10                  15

Ala

<210> SEQ ID NO 3
<211> LENGTH: 17
<212> TYPE: PRT
<213> ORGANISM: Artificial
<220> FEATURE:
<223> OTHER INFORMATION: Cationic antimicrobial peptide
<220> FEATURE:
<221> NAME/KEY: MOD_RES
<222> LOCATION: (17)..(17)
<223> OTHER INFORMATION: AMIDATION

<400> SEQUENCE: 3

Lys Lys Lys Lys Lys Lys Ala Ala Phe Ala Ala Trp Ala Ala Phe Ala
1               5                   10                  15

Ala

<210> SEQ ID NO 4
<211> LENGTH: 21
<212> TYPE: PRT
<213> ORGANISM: Artificial
<220> FEATURE:
<223> OTHER INFORMATION: Cationic antimicrobial peptide
<220> FEATURE:
<221> NAME/KEY: MOD_RES
<222> LOCATION: (21)..(21)
<223> OTHER INFORMATION: AMIDATION

<400> SEQUENCE: 4

Lys Lys Ala Phe Ala Ala Ala Ala Ala Phe Ala Ala Trp Ala Ala Phe
1               5                   10                  15

Ala Lys Lys Lys Lys
            20

<210> SEQ ID NO 5
<211> LENGTH: 17
<212> TYPE: PRT
<213> ORGANISM: Artificial
<220> FEATURE:
<223> OTHER INFORMATION: Cationic antimicrobial peptide
<220> FEATURE:
<221> NAME/KEY: MOD_RES
<222> LOCATION: (17)..(17)
<223> OTHER INFORMATION: AMIDATION

<400> SEQUENCE: 5

Arg Arg Arg Ala Ala Phe Ala Ala Trp Ala Ala Phe Ala Ala Arg Arg
1               5                   10                  15

Arg

<210> SEQ ID NO 6
<211> LENGTH: 25
<212> TYPE: PRT
<213> ORGANISM: Artificial
```

```
<220> FEATURE:
<223> OTHER INFORMATION: Cationic antimicrobial peptide
<220> FEATURE:
<221> NAME/KEY: MOD_RES
<222> LOCATION: (25)..(25)
<223> OTHER INFORMATION: AMIDATION

<400> SEQUENCE: 6

Lys Lys Ala Ala Ala Ala Phe Ala Ala Phe Ala Ala Trp Phe Ala Ala
1               5                   10                  15

Phe Ala Ala Ala Ala Lys Lys Lys Lys
            20                  25

<210> SEQ ID NO 7
<211> LENGTH: 25
<212> TYPE: PRT
<213> ORGANISM: Artificial
<220> FEATURE:
<223> OTHER INFORMATION: Cationic antimicrobial peptide
<220> FEATURE:
<221> NAME/KEY: MOD_RES
<222> LOCATION: (25)..(25)
<223> OTHER INFORMATION: AMIDATION

<400> SEQUENCE: 7

Lys Lys Ala Thr Ala Leu Val Gly Ala Ala Ser Leu Thr Ala Trp Val
1               5                   10                  15

Gly Leu Ala Ser Ala Lys Lys Lys Lys
            20                  25

<210> SEQ ID NO 8
<211> LENGTH: 21
<212> TYPE: PRT
<213> ORGANISM: Artificial
<220> FEATURE:
<223> OTHER INFORMATION: Cationic antimicrobial peptide
<220> FEATURE:
<221> NAME/KEY: MISC_FEATURE
<222> LOCATION: (13)..(13)
<223> OTHER INFORMATION: Xaa can be any hydrophobic amino acid of
      hydropathy value greater than or equal to alanine
<220> FEATURE:
<221> NAME/KEY: MOD_RES
<222> LOCATION: (21)..(21)
<223> OTHER INFORMATION: AMIDATION

<400> SEQUENCE: 8

Lys Lys Ala Phe Ala Ala Ala Ala Phe Ala Ala Xaa Ala Ala Phe
1               5                   10                  15

Ala Lys Lys Lys Lys
            20

<210> SEQ ID NO 9
<211> LENGTH: 16
<212> TYPE: PRT
<213> ORGANISM: Artificial
<220> FEATURE:
<223> OTHER INFORMATION: Cationic antimicrobial peptide
<220> FEATURE:
<221> NAME/KEY: MISC_FEATURE
<222> LOCATION: (12)..(12)
<223> OTHER INFORMATION: Xaa can be any hydrophobic amino acid of
      hydropathy value greater than or equal to alanine
<220> FEATURE:
<221> NAME/KEY: MOD_RES
<222> LOCATION: (16)..(16)
<223> OTHER INFORMATION: AMIDATION
```

```
<400> SEQUENCE: 9

Lys Lys Lys Lys Lys Ala Ala Ala Phe Ala Ala Xaa Ala Ala Phe Ala
1               5                   10                  15

<210> SEQ ID NO 10
<211> LENGTH: 17
<212> TYPE: PRT
<213> ORGANISM: Artificial
<220> FEATURE:
<223> OTHER INFORMATION: Cationic antimicrobial peptide
<220> FEATURE:
<221> NAME/KEY: MISC_FEATURE
<222> LOCATION: (10)..(10)
<223> OTHER INFORMATION: Xaa can be any hydrophobic amino acid of
      hydropathy value greater than or equal to alanine
<220> FEATURE:
<221> NAME/KEY: MOD_RES
<222> LOCATION: (17)..(17)
<223> OTHER INFORMATION: AMIDATION

<400> SEQUENCE: 10

Arg Arg Arg Ala Ala Ala Phe Ala Ala Xaa Ala Ala Phe Ala Arg Arg
1               5                   10                  15

Arg

<210> SEQ ID NO 11
<211> LENGTH: 25
<212> TYPE: PRT
<213> ORGANISM: Artificial
<220> FEATURE:
<223> OTHER INFORMATION: Cationic antimicrobial peptide
<220> FEATURE:
<221> NAME/KEY: MISC_FEATURE
<222> LOCATION: (13)..(13)
<223> OTHER INFORMATION: Xaa can be any hydrophobic amino acid of
      hydropathy value greater than or equal to alanine
<220> FEATURE:
<221> NAME/KEY: MOD_RES
<222> LOCATION: (25)..(25)
<223> OTHER INFORMATION: AMIDATION

<400> SEQUENCE: 11

Lys Lys Ala Ala Ala Ala Phe Ala Ala Phe Ala Ala Xaa Phe Ala Ala
1               5                   10                  15

Phe Ala Ala Ala Ala Lys Lys Lys Lys
            20                  25

<210> SEQ ID NO 12
<211> LENGTH: 25
<212> TYPE: PRT
<213> ORGANISM: Artificial
<220> FEATURE:
<223> OTHER INFORMATION: Cationic antimicrobial peptide
<220> FEATURE:
<221> NAME/KEY: MISC_FEATURE
<222> LOCATION: (15)..(15)
<223> OTHER INFORMATION: Xaa can be any hydrophobic amino acid of
      hydropathy value greater than or equal to alanine
<220> FEATURE:
<221> NAME/KEY: MOD_RES
<222> LOCATION: (25)..(25)
<223> OTHER INFORMATION: AMIDATION

<400> SEQUENCE: 12

Lys Lys Ala Thr Ala Leu Val Gly Ala Ala Ser Leu Thr Ala Xaa Val
1               5                   10                  15

Gly Leu Ala Ser Ala Lys Lys Lys Lys
            20                  25
```

```
<210> SEQ ID NO 13
<211> LENGTH: 25
<212> TYPE: PRT
<213> ORGANISM: Artificial
<220> FEATURE:
<223> OTHER INFORMATION: Cationic antimicrobial peptide
<220> FEATURE:
<221> NAME/KEY: MOD_RES
<222> LOCATION: (25)..(25)
<223> OTHER INFORMATION: AMIDATION

<400> SEQUENCE: 13

Lys Lys Lys Lys Lys Lys Ala Ala Ala Phe Ala Ala Ala Ala Ala Phe
1               5                   10                  15

Ala Ala Trp Ala Ala Phe Ala Ala Ala
            20                  25

<210> SEQ ID NO 14
<211> LENGTH: 17
<212> TYPE: PRT
<213> ORGANISM: Artificial
<220> FEATURE:
<223> OTHER INFORMATION: Cationic antimicrobial peptide
<220> FEATURE:
<221> NAME/KEY: MOD_RES
<222> LOCATION: (17)..(17)
<223> OTHER INFORMATION: AMIDATION

<400> SEQUENCE: 14

Lys Lys Lys Ala Ala Ala Phe Ala Ala Trp Ala Ala Phe Ala Lys Lys
1               5                   10                  15

Lys

<210> SEQ ID NO 15
<211> LENGTH: 17
<212> TYPE: PRT
<213> ORGANISM: Artificial
<220> FEATURE:
<223> OTHER INFORMATION: Cationic antimicrobial peptide
<220> FEATURE:
<221> NAME/KEY: MOD_RES
<222> LOCATION: (17)..(17)
<223> OTHER INFORMATION: AMIDATION

<400> SEQUENCE: 15

Arg Arg Arg Arg Arg Arg Ala Ala Phe Ala Ala Trp Ala Ala Phe Ala
1               5                   10                  15

Ala

<210> SEQ ID NO 16
<211> LENGTH: 17
<212> TYPE: PRT
<213> ORGANISM: Artificial
<220> FEATURE:
<223> OTHER INFORMATION: Cationic antimicrobial peptide
<220> FEATURE:
<221> NAME/KEY: MOD_RES
<222> LOCATION: (17)..(17)
<223> OTHER INFORMATION: AMIDATION

<400> SEQUENCE: 16

Lys Lys Lys Lys Lys Lys Ala Ala Ala Ala Phe Trp Ala Ala Ala Ala
1               5                   10                  15

Phe
```

```
<210> SEQ ID NO 17
<211> LENGTH: 17
<212> TYPE: PRT
<213> ORGANISM: Artificial
<220> FEATURE:
<223> OTHER INFORMATION: Cationic antimicrobial peptide
<220> FEATURE:
<221> NAME/KEY: MOD_RES
<222> LOCATION: (17)..(17)
<223> OTHER INFORMATION: AMIDATION

<400> SEQUENCE: 17

Lys Lys Lys Lys Lys Lys Ala Ala Phe Ala Ala Phe Ala Ala Phe Ala
1               5                   10                  15

Ala

<210> SEQ ID NO 18
<211> LENGTH: 17
<212> TYPE: PRT
<213> ORGANISM: Artificial
<220> FEATURE:
<223> OTHER INFORMATION: Cationic antimicrobial peptide
<220> FEATURE:
<221> NAME/KEY: MOD_RES
<222> LOCATION: (17)..(17)
<223> OTHER INFORMATION: AMIDATION

<400> SEQUENCE: 18

Lys Lys Lys Lys Lys Lys Ala Ala Trp Ala Ala Trp Ala Ala Trp Ala
1               5                   10                  15

Ala

<210> SEQ ID NO 19
<211> LENGTH: 17
<212> TYPE: PRT
<213> ORGANISM: Artificial
<220> FEATURE:
<223> OTHER INFORMATION: Cationic antimicrobial peptide
<220> FEATURE:
<221> NAME/KEY: MISC_FEATURE
<222> LOCATION: (7)..(8)
<223> OTHER INFORMATION: Xaa can be any amino acid of hydropathy value
      greater than or equal to alanine
<220> FEATURE:
<221> NAME/KEY: MISC_FEATURE
<222> LOCATION: (10)..(11)
<223> OTHER INFORMATION: Xaa can be any amino acid of hydropathy value
      greater than or equal to alanine
<220> FEATURE:
<221> NAME/KEY: MISC_FEATURE
<222> LOCATION: (13)..(14)
<223> OTHER INFORMATION: Xaa can be any amino acid of hydropathy value
      greater than or equal to alanine
<220> FEATURE:
<221> NAME/KEY: MISC_FEATURE
<222> LOCATION: (16)..(17)
<223> OTHER INFORMATION: Xaa can be any amino acid of hydropathy value
      greater than or equal to alanine
<220> FEATURE:
<221> NAME/KEY: MOD_RES
<222> LOCATION: (17)..(17)
<223> OTHER INFORMATION: AMIDATION

<400> SEQUENCE: 19

Lys Lys Lys Lys Lys Lys Xaa Xaa Phe Xaa Xaa Trp Xaa Xaa Phe Xaa
1               5                   10                  15

Xaa
```

```
<210> SEQ ID NO 20
<211> LENGTH: 17
<212> TYPE: PRT
<213> ORGANISM: Artificial
<220> FEATURE:
<223> OTHER INFORMATION: Cationic antimicrobial peptide
<220> FEATURE:
<221> NAME/KEY: MISC_FEATURE
<222> LOCATION: (8)..(8)
<223> OTHER INFORMATION: Xaa can be any amino acid of hydropathy value
      greater than or equal to alanine
<220> FEATURE:
<221> NAME/KEY: MISC_FEATURE
<222> LOCATION: (11)..(11)
<223> OTHER INFORMATION: Xaa can be any amino acid of hydropathy value
      greater than or equal to alanine
<220> FEATURE:
<221> NAME/KEY: MISC_FEATURE
<222> LOCATION: (13)..(13)
<223> OTHER INFORMATION: Xaa can be any amino acid of hydropathy value
      greater than or equal to alanine
<220> FEATURE:
<221> NAME/KEY: MISC_FEATURE
<222> LOCATION: (16)..(16)
<223> OTHER INFORMATION: Xaa can be any amino acid of hydropathy value
      greater than or equal to alanine
<220> FEATURE:
<221> NAME/KEY: MOD_RES
<222> LOCATION: (17)..(17)
<223> OTHER INFORMATION: AMIDATION

<400> SEQUENCE: 20

Lys Lys Lys Lys Lys Lys Ala Xaa Phe Ala Xaa Trp Xaa Ala Phe Xaa
1               5                   10                  15

Ala

<210> SEQ ID NO 21
<211> LENGTH: 17
<212> TYPE: PRT
<213> ORGANISM: Artificial
<220> FEATURE:
<223> OTHER INFORMATION: Cationic antimicrobial peptide
<220> FEATURE:
<221> NAME/KEY: MISC_FEATURE
<222> LOCATION: (7)..(8)
<223> OTHER INFORMATION: Xaa can be A or L
<220> FEATURE:
<221> NAME/KEY: MISC_FEATURE
<222> LOCATION: (10)..(11)
<223> OTHER INFORMATION: Xaa can be A or L
<220> FEATURE:
<221> NAME/KEY: MISC_FEATURE
<222> LOCATION: (13)..(14)
<223> OTHER INFORMATION: Xaa can be A or L
<220> FEATURE:
<221> NAME/KEY: MISC_FEATURE
<222> LOCATION: (16)..(17)
<223> OTHER INFORMATION: Xaa can be A or L
<220> FEATURE:
<221> NAME/KEY: MOD_RES
<222> LOCATION: (17)..(17)
<223> OTHER INFORMATION: AMIDATION

<400> SEQUENCE: 21

Lys Lys Lys Lys Lys Lys Xaa Xaa Phe Xaa Xaa Trp Xaa Xaa Phe Xaa
1               5                   10                  15

Xaa
```